US011369699B2

(12) United States Patent
Alphandery

(10) Patent No.: US 11,369,699 B2
(45) Date of Patent: Jun. 28, 2022

(54) MAGNETIC NANOPARTICLES FOR DESTROYING PATHOLOGICAL CELLS IN AN INDIVIDUAL

(71) Applicant: NANOBACTERIE, Paris (FR)

(72) Inventor: Edouard Alphandery, Paris (FR)

(73) Assignee: NANOBACTERIE, Paris (FR)

( * ) Notice: Subject to any disclaimer, the term of this patent is extended or adjusted under 35 U.S.C. 154(b) by 161 days.

(21) Appl. No.: 16/845,412

(22) Filed: Apr. 10, 2020

(65) Prior Publication Data

US 2020/0237933 A1 Jul. 30, 2020

Related U.S. Application Data

(63) Continuation of application No. 15/615,206, filed on Jun. 6, 2017, now Pat. No. 10,660,975.

(30) Foreign Application Priority Data

Oct. 21, 2016 (EP) .................................. 16290202
Dec. 14, 2016 (EP) .................................. 16290233

(51) Int. Cl.
| | | |
|---|---|---|
| *A61N 2/00* | (2006.01) | |
| *A61K 49/18* | (2006.01) | |
| *A61K 35/74* | (2015.01) | |
| *A61K 41/00* | (2020.01) | |
| *A61K 47/69* | (2017.01) | |
| *A61K 33/26* | (2006.01) | |
| *A61K 51/12* | (2006.01) | |
| *A61N 1/40* | (2006.01) | |
| *A61N 5/10* | (2006.01) | |
| *A61N 5/00* | (2006.01) | |
| *B82Y 5/00* | (2011.01) | |

(52) U.S. Cl.
CPC .......... *A61K 49/1887* (2013.01); *A61K 33/26* (2013.01); *A61K 35/74* (2013.01); *A61K 41/00* (2013.01); *A61K 41/0052* (2013.01); *A61K 47/6901* (2017.08); *A61K 47/6923* (2017.08); *A61K 47/6929* (2017.08); *A61K 51/1255* (2013.01); *A61N 1/406* (2013.01); *A61N 5/1001* (2013.01); *A61N 2/00* (2013.01); *A61N 5/00* (2013.01); *B82Y 5/00* (2013.01)

(58) Field of Classification Search
CPC ................ A61K 33/26; A61K 41/0052; A61K 47/6929; A61K 49/1887; A61N 1/406; A61N 5/00; A61N 5/1001; A61N 2/00
See application file for complete search history.

(56) References Cited

U.S. PATENT DOCUMENTS

2007/0231393 A1 10/2007 Ritter
2014/0348825 A1 11/2014 Friedman
2016/0143859 A1 5/2016 Brossel

OTHER PUBLICATIONS

Edouard Alphandery et al.: "Chains of Magnetosomes Extracted from AMB-1 Magnetotactic Bacteria for Application in Alternative Magnetic Field Cancer Therapy", vol. 5, No. 8, 6279-6296, 2011.

*Primary Examiner* — Christine H Matthews
(74) *Attorney, Agent, or Firm* — Maier & Maier, PLLC

(57) ABSTRACT

A composition including magnetic nanoparticles for use in the treatment of a tissue volume including pathological cells in an individual, wherein a portion only of the tissue volume is occupied by the magnetic nanoparticles upon administration of the composition to the individual and the magnetic nanoparticles are excited by radiation.

25 Claims, 2 Drawing Sheets

MAGNETIC NANOPARTICLES FOR DESTROYING PATHOLOGICAL CELLS IN AN INDIVIDUAL

CROSS-REFERENCE TO RELATED APPLICATIONS

This is a Continuation application of a U.S. patent application Ser. No. 15/615,206 entitled "MAGNETIC NANOPARTICLES FOR DESTROYING PATHOLOGICAL CELLS IN AN INDIVIDUAL" filed on Jun. 6, 2017 which claims priority to European Patent Application No. 16290233.2 filed on Dec. 14, 2016 and European Patent Application No. 16290202.7 filed on Oct. 21, 2016, the contents of which are all incorporated herein by reference.

FIELD OF THE INVENTION

The present invention relates to method of treatment of pathological cells, in particular tumor cells, by using magnetic nanoparticles.

TECHNICAL BACKGROUND

It has previously been shown that it was possible to destroy tumors by administering nanoparticles to tumors and by heating these nanoparticles by the application of an alternating magnetic field (Alphandery et al. (2001) *ACSNano* 5:6279-6296).

Under these conditions, efficient tumor destruction is generally achieved when nanoparticles are homogenously distributed within the whole tumor volume.

However, this often requires administering a high quantity of nanoparticles. Besides, heating is then such that surrounding healthy tissues may be affected.

SUMMARY OF THE INVENTION

The present invention arises from the unexpected finding, by the present inventors, that magnetic nanoparticles could exert a therapeutic effect upon excitation by radiations without occupying the totality of a tissue volume comprising pathological cells, such as a tumor, to be treated. Moreover, the inventors could observe a therapeutic effect even without observing a significant increase in temperature of the tissue volume. The inventors have also unexpectedly evidenced that magnetic nanoparticles could attract immune cells to the tissue volume and/or that they destroyed blood vessels within the tissue volume.

As such, the present invention relates to a composition comprising magnetic nanoparticles for use in the treatment of a tissue volume comprising pathological cells in an individual, wherein a portion only of the tissue volume is occupied by the magnetic nanoparticles upon administration of the composition to the individual and the magnetic nanoparticles are excited by radiations.

The present invention also relates to a method of treatment of a tissue volume comprising pathological cells in an individual, comprising administering the individual an effective amount of a composition comprising magnetic nanoparticles, wherein a portion only of the tissue volume is occupied by the magnetic nanoparticles upon administration of the composition to the individual and the magnetic nanoparticles are excited by radiations.

DESCRIPTION OF THE FIGURES

FIG. 1a

FIG. 1a is a representation of a body site of the individual just after administration of the composition at $t_0$ corresponding to the tissue volume, and the pathological, healthy and origin sites which respectively comprise the pathological, healthy and targeting cells (i e immune cells), respectively, as well as the administration site of the composition comprising an association of magnetic nanoparticles and an immune attractant.

FIG. 1b

FIG. 1b is a representation of the body site just after irradiation at time t showing the distribution of pathological, healthy, and targeting cells (i e immune cells) as well as that of the association or composition within the pathological, and healthy site, the administration site and association diffusion region. The targeting cells are migrating from the origin site to the target site, which location corresponds to that designated by the wide arrows.

FIG. 2

FIG. 2 is a schematic representation of the direct and indirect mechanisms taking place in heated and non-heated regions, respectively. Heated and non-heated regions can be defined as the regions where temperature increase can be measured and not measured, respectively.

DESCRIPTION OF THE INVENTION

Figure 1:
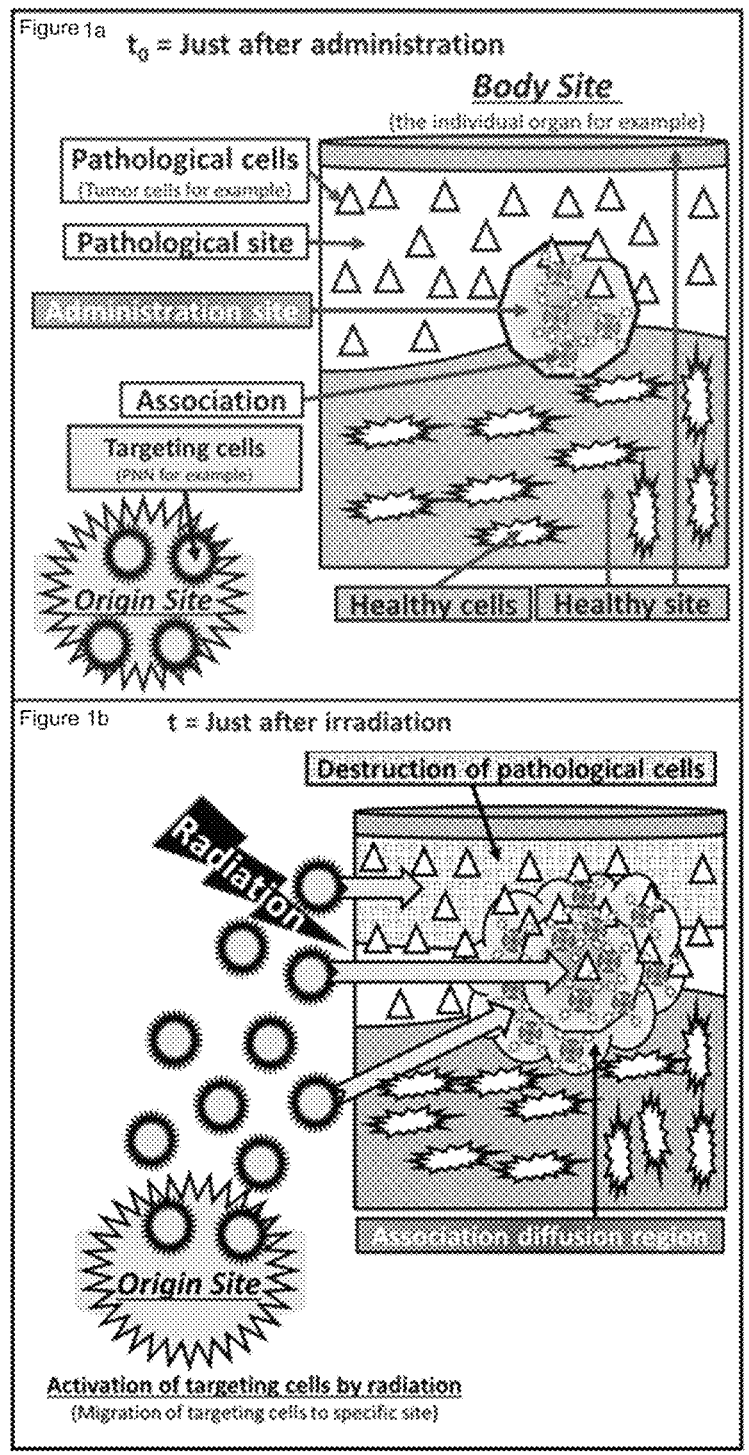
FIGS. 1a, 1b and 2 are schematic diagrams that summarize some aspects of the invention.
Figure 2:
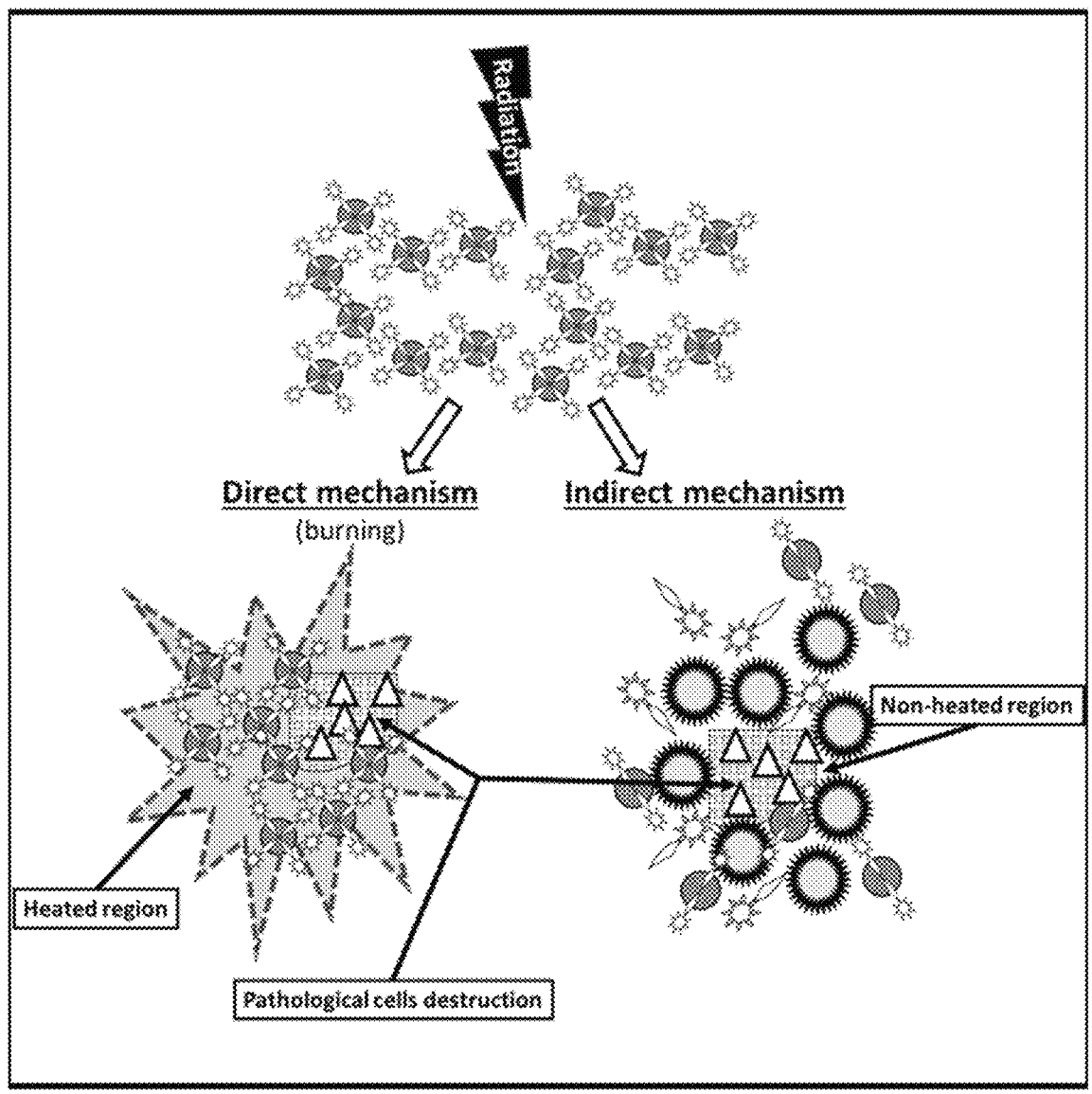

Nanoparticles According to the invention, the magnetic nanoparticle can be characterized by at least one of the following properties: i), a coercivity, $H_c$, which is larger than $10^{-4}$, $10^{-3}$, $10^{-2}$, $10^{-1}$, 1, 10, $10^2$, $10^3$, $10^4$, or $10^5$ Oe, or by, ii), a ratio between remanent and saturating magnetization, $M_r/M_s$, which is larger than 0.001, 0.01, 0.1, 0.2, 0.3, 0.4, 0.5, 0.6, 0.7, 0.8, or 0.9, or by, iii), a saturating magnetization, $M_s$ which is larger than 0.1, 1, 10, or 100 emu/g. $H_c$ and/or $M_r/M_s$ and/or $M_s$ is/are preferentially non-zero when it/they is/are measured at a higher temperature than 0, 0.1, 1, 2, 5, 10, 100, 200, 300, 400, 500, 700, or 1000 K.

In an embodiment of the invention, the magnetic nanoparticles comprise at least 1, 10, $10^2$, $10^3$, $10^4$, $10^5$, $10^6$, $10^7$, $10^8$, or $10^9$ magnetic or metallic atom(s). Such atom(s) can be iron, zinc, manganese, cobalt, nickel. Such atom(s) preferentially possess(es) a low toxicity or is/are combined with other atom(s) to yield a low toxicity. The magnetic nanoparticles can possess a non-zero magnetic moment and/or a stable magnetic moment. The magnetic nanoparticles can be made of a metal oxide, such as an iron oxide, in particular maghemite or magnetite.

In one embodiment of the invention, the magnetic nanoparticles can be organized in chains containing more, or less, than 2, 3, 4, 5, 6, 7, 8, 9, 10, 15, 20, 25, 50, 100, 200, 500, or 1000 magnetic nanoparticles. An organization in chain can be due to at least one of the following properties: i) two or more magnetic nanoparticles bound together, ii), two or more magnetic nanoparticles having crystallographic directions orientated in the direction of the chain elongation, i.e. preferentially forming an angle between their crystallographic directions and the direction of the chain elongation of less than 85, 80, 75, 70, 60, 50, 45, 30, or 20 degrees, iii), two or more magnetic nanoparticles having their easy axes of magnetization orientated in the direction of the chain elongation, i.e. preferentially forming an angle between their easy axes and the direction of the chain elongation of less than 85, 80, 75, 70, 60, 50, 45, 30, or 20 degrees. In some cases, the organization in chains can be observed by electron transmission microscopy or by electron holography. It can be observed when the magnetic nanoparticles are in suspension, in a matrix, or dried or when the magnetic nanoparticles are in a living organism or outside of a living organism.

Preferably, the magnetic nanoparticles according to the invention are diamagnetic, superparamagnetic, ferromagnetic or ferrimagnetic nanoparticles. More preferably, the magnetic nanoparticles according to the invention are iron oxide ferrimagnetic nanoparticles, such as magnetosomes.

The magnetic nanoparticle according to the invention can be synthesized chemically or be produced by living organisms, intracellularly or extracellularly, preferably by a bacterium, more preferably by a magnetotactic bacterium. As intended herein, the magnetic nanoparticle can be said to be produced by a living organism when at least one step in its manufacture process involves a contact with or a processing by the producing living organism. As intended herein also, a magnetic nanoparticle, which is produced by a magnetotactic bacterium is called a magnetosome. As intended herein also, a magnetic nanoparticle, which is not produced by a magnetotactic bacterium but has similar properties than a magnetosomes, i.e. that has values of $H_C$, $M_r/M_s$, SAR and/or $M_s$ that are not more than 90%, 70%, 50%, or 25% different from that/those of the magnetosomes and/or that leads to a chain arrangement, can be assimilated to a magnetosome.

Preferably, the magnetotactic bacterium according to the invention is selected from the group consisting of a *Magnetospirillum magneticum* strain such as AMB-1, a magnetotactic coccus strain such as MC-1, a facultative anaerobic vibrios strains such as MV-1, MV-2 and MV-4, a *Magnetospirillum magnetotacticum* strain MS-1, a *Magnetospirillum gryphiswaldense* strain MSR-1, a facultative anerobic magnetotactic spirillum, such as *Magnetospirillum magneticum* strain MGT-1, an obligate anaerobe such as *Desulfovibrio magneticus* RS-1.

Preferably, the magnetic nanoparticles according to the invention are non-pyrogenic. In this case, they preferably contain less than 10000, 1000, 100, or 10 EU (endotoxin unit) per mg of magnetic nanoparticle.

Preferably, where the magnetic nanoparticles according to the invention are produced by a living organism, they contain a percentage of carbon originating from the producing living organism, of less than 90, 80, 70, 60, 50, 25, 10, 5, 2, 1, or 0.5% expressed as the weight or number of atoms of carbon contained in the magnetic nanoparticle and/or substance respectively divided by the total weight or total number of atoms of the magnetic nanoparticle and/or substance.

Upon their excitation by radiations the magnetic nanoparticles according to the invention may enter into movement, produce heat, release substances bound to them and/or produce free radicals.

Preferably, the free radicals are made of reactive oxygen species (ROS) and reactive nitrogen species (RNS). Examples of free radicals include superoxide, oxygen radical, hydroxyl, alkoxyradical, peroxyl radical, nitric oxide, nitrogen monoxide, and nitrogen dioxide.

Preferably, the specific absorption rate (SAR) of the magnetic nanoparticles in the tissue volume upon their administration to the individual yields a power of at least $10^{-3}$, $5\ 10^{-3}$, $10^{-2}$, $5.6\ 10^{-2}$, $10^{-2}$ or $10^{-1}$ W per cm³ of the tissue volume. Advantageously, this power is the minimal power yielding a therapeutic effect without a significant increase is temperature is observed.

Preferably, the specific absorption rate (SAR) of the magnetic nanoparticles in the tissue volume upon their administration to the individual yields a power of $10^{-2}$, $10^{-1}$, 1, 10, 100, $1.7\ 10^3$, $10^4$ or $10^5$ W per cm³ of the tissue volume at the most. Advantageously, this power is the maximal power yielding a therapeutic effect without a significant increase is temperature is observed.

Preferably, the SAR per cm³ of the tissue volume corresponds to: SAR.Q/V, where the SAR is that of the magnetic nanoparticles, Q is the quantity of nanoparticles in the tissue volume and V is the tissue volume. The SAR, preferentially expressed in W per gram of iron contained in magnetic nanoparticles, can be estimated using the relation SAR=$C_V$ ($\Delta T/\delta t)/C_{Fe}$, where $C_v$ is the heat capacity of the medium containing the magnetic nanoparticles, $\Delta T/\delta t$ is the slope at the origin of the variation of temperature with time upon excitation by radiation of the magnetic nanoparticle and $C_{Fe}$ is the concentration in iron of the magnetic nanoparticles. The SAR is preferentially measured at a frequency and/or strength of the magnetic field that can be used for magnetic hyperthermia without inducing toxicity such as that leading to whole body heating. This frequency is preferentially lower than $10^4$, $10^3$, 500, 250, or 100 kHz, preferentially larger than 0.1, 10, 20, 50, or 100 kHz. The magnetic field strength is preferentially larger than the coercivity of the magnetic nanoparticles, preferentially larger than $10^{-3}$, $10^{-2}$, $10^{-1}$, 1, or 10 mT, preferentially lower than $10^3$, $10^2$, or 10 T. Preferably, the above SAR is a theoretical SAR, SAR (theo), of the magnetic nanoparticles, which is preferentially measured in adiabatic conditions, at high magnetic nanoparticle concentrations, i.e. larger than $10^{-2}$, $10^{-1}$, 1, 5, 10, or 100 mg/mL, in a medium such as water or a gel, in a volume smaller than $10^3$, $10^2$, 10, 1, $10^{-1}$, $10^{-2}$, or $10^{-3}$ mL, and/or in conditions that enable to yield the maximum SAR that can be reached with the magnetic nanoparticles, preferentially using an alternating magnetic field with a fixed strength and frequency. The SAR can also be an experimental SAR, SAR(exp), of the magnetic nanoparticles, which is preferentially measured in vivo or in conditions mimicking in vivo conditions. The quantity of nanoparticles in the tissue volume, Q, can correspond to the quantity of nanoparticles administered in the tissue volume times the percentage of nanoparticles in the tissue volume.

Radiations

According to the invention, the radiations can be waves, such electromagnetic waves or sound waves, or particles, without or with a weight, preferentially in movement.

Preferably, the radiations are selected from the group consisting of a magnetic field, a laser, an ionizing radiation and a sound radiation.

Preferably also the radiations are alpha, beta, gamma, X-ray, neutron, proton, electron, ion, neutrino, muon, meson, photon particles or radiations.

Preferably also, the radiations are ultra-sounds or radiofrequencies.

Preferably also, the radiations are a magnetic field, more preferably with a strength higher or lower than 1 µT, 10 µT, 100 µT, 1 mT, 10 mT, or 100 mT, or 1 T, or 5 T, or 10 T, or 100 T. More preferably also the radiations are a magnetic field with a strength that varies spatially by more, or less, than 1 µT per mm, or 10 µT per mm, or 100 µT per mm, or 1 mT per mm, or 10 mT per mm, or 100 mT per mm, or 1 T per mm, or 5 T per mm, or 10 T per mm, or 100 T per mm.

Preferably, the radiations according to the invention have a frequency of oscillation of more, or less, than 1 MHz, or 1000 kHz, or 100 kHz, or 10 kHz, or 1 kHz, or 0.1 kHz, or 0.01 kHz, or 0.001 kHz. In this case, the radiations can be an oscillating or alternating magnetic field, a magnetic field with a strength that varies as a function of time and/or space with such frequency.

Preferably, the radiations according to the invention have a power larger or lower than 0.01 W, or 0.1 W, or 1 W, or 10 W, or 100 W, or 1000 W, or 10000 W, or 100000 W.

Preferably, the radiations according to the invention generate free radicals, in particular as defined above.

Preferably, the radiation has a power, strength, and/or frequency, which is sufficient to activate magnetic nanoparticles, preferentially to heat magnetic nanoparticles, preferentially a strength higher than $10^{-3}$, $10^{-2}$, $10^{-1}$, 1, or 10 mT, preferentially a frequency larger than $10^{-3}$, $10^{-2}$, $10^{-1}$, 10, 50, 100, or 200 KHz, preferentially a power higher than $10^{-6}$, $10^{-3}$, $10^{-1}$, 1, 10, or $10^3$ Watt or Watt per cm$^3$ of tissue volume.

Preferably, the radiation has a power, strength, and/or frequency, which is/are kept below a certain threshold to avoid toxicity, such as that induced by Foucault currents or by heat produced outside of the tissue volume, preferentially a strength lower than $10^{-3}$, $10^{-2}$, $10^{-1}$, 1, 10, 100, or 1000 mT, preferentially a frequency lower than $10^{-3}$, $10^{-2}$, $10^{-1}$, 10, 50, 100, 200, 1000, or 10000 KHz, preferentially a power lower than $10^{-6}$, $10^{-3}$, $10^{-1}$, 1, 10, $10^3$, $10^6$, or $10^9$ Watt or Watt per cm$^3$ of tissue volume.

Preferably, the excitation by radiation of the magnetic nanoparticles is continuous, i.e. it is preferentially not stopped during a period of time of more, or less, than $10^{-6}$, $10^{-3}$, $10^{-1}$, 1, or $10^3$ seconds.

Preferably, the excitation by radiation of the magnetic nanoparticles takes place in less than 90%, 70%, 60%, 50%, 40%, 30%, 20%, 10%, 5%, 2%, 1%, 0.1% of the tissue volume.

Immune Attractant

Preferably, at least one immune-attractant is bound or associated to the magnetic nanoparticles, preferentially releasably, and is activated or released upon excitation of the nanoparticles by radiations.

As intended herein an immune-attractant relates to a substance which attracts immune cells, optionally upon excitation of the nanoparticles by radiations.

The immune cells which may be attracted by the immune-attractant according to the invention may notably be selected from those belonging to the innate or adaptive immune system, in particular from the group consisting of an antigen presenting cell (APC), a basophil, a dendritic cell, an eosinophil, a granulocyte, a killing cell, a leukocyte, a lymphocyte, a macrophage, a mast cell, a natural killer, a neutrophil, a phagocyte, a B or T cell, such as a CD8+T lymphocyte, a helper cell (Th1 or Th2), or a gamma delta T cell.

More preferably, the immune-attractant is a pathological cell, an immune cell or part of an immune cell, an immune substance or part of an immune substance, where an immune substance can be one or more amino acids, an acid such as uric acid, an antigen, an antibody, a base such as NaOH, a cluster such as a cluster of differentiation, CpG, a complex such as a major histocompatibility complex, MHC, MHC-1, MHC-2, MHC-3, a cytokine, a cytoplasmic molecule such as HMGB1, DNA, preferentially bacterial DNA, an endotoxin, an enzyme, flagellin, glycan, glycoconjugate, a ligand such as a ligand expressed at the surface of stressed cells, an interleukin, a lipid, a lipopolysaccharide (LPS), a lipoteichoic acid, a protein, a stress protein, a heat shock protein, a formylated protein, RNA, a pathogen-associated molecular pattern (PAMP), peptidoglucan, a receptor, such as a molecular pattern recognition receptor (PRR), a specific Toll-like receptor (TLR), a NOD-like receptor (NLR), a RIG-I-like receptor (RGR), or a C-type lectin receptor (CLR), a substance not belonging to the individual to be treated with the composition, an inactivated or attenuated microorganism, an inactivated toxic compound that leads to the appearance of the pathological cell, a biological substance, a subunit of protein, lipid, DNA, RNA, a substance produced by a plant, an animal, a bacterium, a fungus, a eukaryotic or prokaryotic cell, a polysaccharide, or a recombinant vector, a vaccine component or vaccine adjuvant, or an equivalently active substance to those listed above that is non-toxic such as MPLA, which is a non-toxic equivalent of LPS.

Preferably, the immune-attractant is linked to the magnetic nanoparticle by weak bonds, which can be hydrogen bonds or van der Waals interactions. Alternatively, the immune-attractant may be linked to the magnetic nanoparticle by strong bonds, which can be ionic or covalent bonds.

Coating

Preferably, the magnetic nanoparticles are coated by a coating that stabilizes the magnetic nanoparticles in the composition, preferentially to facilitate its administration. The coating may also prevent the aggregation of the magnetic nanoparticle, enable its uniform heating or yield an organization of magnetic nanoparticles in a different geometry than a cluster or aggregate, preferentially yield an anisotropic structure such as a chain.

Preferably, the magnetic nanoparticles are coated by a cytotoxic coating. A cytotoxic coating can be more cytotoxic towards pathological than healthy cells or be cytotoxic towards pathological cells and not cytotoxic towards healthy cells. It may also correspond to a coating that is more or less cytotoxic when it is: i), associated to the nanoparticles than when it is free, ii) excited by radiation than when it is not excited by radiation, or iii) internalized in pathological cells or localized at the surface of these cells than when it is not internalized in these cells or not localized at the surface of these cells.

Preferably, the coating has a thickness of more, or less, than 0.5, 1, 2, 3, 4, 5, 6, 7, 8, 9, 10, 15, 20, 25, 30, 40, 50, 75, 100, 250, 500, or 1000 nm.

Preferably, the coating, optionally the cytotoxic coating, is poly-lysine, a polysaccharide, a fatty acid, a phospholipid, a lipid, a polymer, a polymer of amino acids, polymeric or non-polymeric silica, a aliphatic amine polymer, an acidic, basic, oxidized, reduced, neutral, positively charged, negatively charged derivative of these compounds, or a combination of several of these compounds or derivatives. The cytotoxic coating may also contain at least one cytotoxic function, such as a function selected from the group consisting of phosphoric acids, carboxylic acids, sulfonic acids, esters, amides, ketones, alcohols, phenols, thiols, amines, ethers, sulfides, acid anhydrides, acyl halides, amidines, nitriles, hydroperoxides, imines, aldehydes, peroxides, an acidic, basic, oxidized, reduced, neutral, positively charged, negatively charged derivative of these compounds, or a combination of several of these compounds or their derivatives.

As intended herein, the coating is preferably said to be cytotoxic when it yields a percentage of cell inhibition, or a percentage of dead cells in the presence of the composition, of more, or less, than 90%, 75%, 50%, 30%, 20%, 10%, 5%, or 2%, preferably at a concentration in nanoparticles of more, or less, than 0.01, 0.1, 1, or 10 mg/mL, preferably at a cellular concentration of more, or less, than 10, $10^2$, $10^3$, $10^5$, or $10^9$ cells per mL, preferably following an incubation time of more, or less, than 0.01, 0.1, 1, 10, 24, 48, 72, $10^2$, or $10^3$ hours.

Individual

The individual according to the invention is a living organism, preferably a metazoan, preferably an animal, even more preferably a mammal and most preferably a human, in particular an adult, an adolescent, or a child.

Tissue Volume

The pathological cells according to the invention weaken, or destroy, partly or fully, cells, tissues or organs of the individual. The pathological cells according to the invention may notably be cancer or tumor cells, viruses or pathogenic bacteria.

As intended herein the tissue volume relates to a part of the individual's body which may comprise all or part of one tissue or of several different tissues.

Preferably, the tissue volume may be associated to a tissue surface, for example when one collects or examines a thin section of tissue volume, which is more preferably thinner than 10, 1, or 0.1 µm.

Preferably, the tissue volume comprising pathological cells is a tumor or cancer, more preferably selected from the group consisting of adrenal, anal, bile duct, bladder, bone, brain, breast, cervical, colon/rectum, endometrial, esophagus, eye, gallbladder, kidney, laryngeal and hypopharyngeal, leukemia, liver, lung, nasal cavity and paranasal sinus, nasopharyngeal, neuroblastoma, non-hodgkin lymphoma, oral cavity and oropharyngeal, osteosarcoma, ovarian, pancreatic penile, prostate, retinoblastoma, rhabdomyosarcoma, salivary gland, sarcoma, skin, small intestine, stomach, testicular, thymus, thyroid, uterine sarcoma, vaginal, and vulvar cancer, and waldenstrom macroglobulinemia wilms tumor, castleman disease ewing family of tumor, gastrointestinal carcinoid tumor, gastrointestinal stromal tumor, myelodysplastic syndrome pituitary tumor, and a cancerous disease such as gestational trophoblastic disease, hodgkin disease, kaposi sarcoma, malignant mesothelioma, and multiple myeloma.

Administration

Preferably, the composition according to the invention is administered into or near the tissue volume to be treated, i.e. preferentially less than 100, 50, 25, 10, 5, 2, or 1 cm away from the tissue volume.

Alternatively, the composition may be administered at distance from the tissue volume, i.e. preferentially more than 100, 50, 25, 10, 5, 2, or 1 cm away from the tissue volume, for example when the composition targets the tissue volume or when the composition contains the pathological cells to be treated.

Preferably, the composition is administered following at least one of the following different routes: gastrointestinal, enteral, through the gastrointestinal tract, through the intestine, through or within one of the organs of an individual, orally, into the rectum, in the stomach, sublingual, buccal, enteral, systemically, topical, epidural, intracerebral, intracerebroventricular, transderma, extra-amniotic, nasal, intraarterial, intraarticular, intracardiac, intravenous, intracavernous, intradermal, intralesional, intramuscular, intraocular, into the bone marrow, intraperitoneal, intrathecal, intrauterine, intravitreal, subcutaneous, transdermal, transmucosal, or intratumoraly.

Preferably, the magnetic nanoparticles are excited by radiations a first time and at least another time, without re-administration of magnetic nanoparticles occurring after the first time.

Preferably, the first excitation and the at least another excitation are separated for more than 1, 2, 6, 12, 24, 48, or 72 hours, 4, 7, 15, or 30 days, 2, 6, or 12 months, 2, 5, or 10 years.

Preferably also, the excitation by radiation is repeated more than 1, 2, 3, 4, 5, 6, 7, 8, 9, 10, 11, 12, 13, 14, 15, 20, 25, 30, 40, 50, 75, or 100 time(s), preferably without re-administration of the composition or magnetic nanoparticles according to the invention. Preferably also, the excitation by radiation is repeated less than 3, 4, 5, 6, 7, 8, 9, 10, 11, 12, 13, 14, 15, 20, 25, 30, 40, 50, 75, or 100 time(s), preferably without re-administration of the composition or magnetic nanoparticles according to the invention.

Preferably, the composition comprises at least one pharmaceutically acceptable vehicle in addition to the magnetic nanoparticles. Such vehicle can favor the administration, contact, or interaction, of the magnetic nanoparticles to or with the individual. The vehicle may also reduce the toxicity or improve the efficacy of the magnetic nanoparticles. The vehicle may also favor the contact, interaction, mixing, or administration, of the magnetic nanoparticles with or to the individual. Preferably, the vehicle is an excipient, an adjuvant, a cream, a liquid, a gas, or a solid matrix.

Preferably, the composition also comprises pathological cells or subunits thereof, in particular antigenically active subunits thereof. Such a composition is then useful as a vaccine composition.

Preferably, the composition is a pharmaceutical composition, a vaccine composition, a medicament or a medical device.

Occupation

Preferably less than 95%, 90%, 70%, 60%, 55%, 50%, 45%, 40%, 35%, 30%, 25%, 20%, 15%, or 10% in volume of the tissue volume is occupied by the magnetic nanoparticles. The percentage in volume of the tissue volume is calculated by measuring the volume occupied by the magnetic nanoparticles in the tissue and the tissue volume, and by dividing the volume occupied by the magnetic nanoparticles in the tissue by the tissue volume. The volume occupied by the magnetic nanoparticles in the tissue may correspond to that comprising the majority of the administered magnetic nanoparticles. The magnetic nanoparticles and/or the tissue volume may preferentially be imaged using optical or electron microscopy, histology, magnetic imaging, MRI, a scanner, ultrasound, radiology, or echography. In some cases, it may be possible to collect the tissue volume and to measure, for example by histology, the surface occupied by the magnetic nanoparticle in a section of the tissue volume. This percentage may also correspond to the surface occupied by the magnetic nanoparticles in the tissue volume divided by the surface of the tissue volume, preferentially using one or several sections of the collected tissue volume, preferentially before or after excitation by radiation. In some cases, it is possible to obtain a qualitative or quantitative estimate of the volume or surface occupied by the magnetic nanoparticles and tissue volume. For example, the surface or volume containing the magnetic nanoparticles and the tissue volume such as a tumor may be observed by variations between the surface or volume containing the magnetic nanoparticles or tissue and the surface or volume not containing the magnetic nanoparticles or tissue volume. These variations can correspond to changes in color, type or number of cell, magnetic or optical properties.

Preferably, the residence time of the magnetic nanoparticles is defined as the time during which the magnetic nanoparticles remain within the tissue volume. It may be measured by measuring the concentration of the composition in the tissue volume at different times following administration to the individual, optionally following excitation of the magnetic nanoparticles by radiations.

Preferably, the residence time lasts longer than $10^{-9}$, $10^{-8}$, $10^{-7}$, $10^{-6}$, $10^{-5}$, $10^{-4}$, $10^{-3}$, $10^{-2}$, $10^{-2}$, $10^{-1}$, 1, 10, $10^2$, $10^3$, $10^4$, $10^5$, $10^6$, $10^7$, $10^8$, or $10^9$ seconds. In some cases, it can last longer than 1, 2, 5, 10, $10^2$, $10^3$, $10^4$, $10^5$, $10^6$, $10^7$, $10^8$, $10^9$, or $10^{10}$ hours. In some cases, the residence time can correspond to the time during which more than 1%, 2%, 5%, 10%, 20%, 40%, 60%, 80%, or 90% of the administered composition remains in the tissue volume.

As will be clear to one of skill in the art, the residence time is sufficiently long to enable treatment. Preferably, the residence time is sufficiently long for the tissue volume to comprise more than 1%, 2%, 5%, 10%, 25%, 50%, 75%, 80%, or 95% of the administered composition, in particular 1, 5, 10, or 60 seconds, 2, 5, 15, 30, or 60 minutes, 2, 5, 10, or 24 hours, 2, 5, 15, or 30 days, 2, 6, or 12 months, or 2, 5, or 10 years following administration of the composition.

Preferably, the magnetic nanoparticles occupy a peripheral portion of the tissue volume. In other words, the magnetic nanoparticles preferably do not occupy a central portion of the tissue volume. Preferably, the peripheral portion of the tissue volume represents at least 10%, 20%, 30%, 40%, or 50% in volume of the tissue volume. Preferably also, the peripheral portion of the tissue volume represents less than 10%, 20%, 30%, 40%, or 50% in volume of the tissue volume.

Preferably, the quantity of magnetic nanoparticles in the tissue volume can be larger, or lower, than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, $10^8$, or $10^9$ mg in iron per mm$^3$ or mm$^2$ or mm.

Mechanism of Action

As will be clear to one of skill in the art, excitation of the magnetic nanoparticles by the radiations directly and/or indirectly results in the treatment or destruction of the pathological cells in the individual.

Preferably, the excitation of the magnetic nanoparticles by radiations results in a larger number of pathological cells than healthy cells being destroyed, preferably 1.1, 1.2, 2, 5, 10, 50, 100, $10^3$, or $10^5$ times more pathological cells than healthy cells destroyed.

As intended herein, pathological cell treatment or destruction can be partial or total and can be associated with a loss of activity, a decrease in proliferation, an inhibition, an apoptotic or necrotic death, of these pathological cells. Pathological cell treatment or destruction can also be associated with the destruction of the cell membrane or of any type of organelle, DNA, RNA, protein, amino acid, nucleic acid, lipid, or biological material, produced by or originating from this cell.

Preferably, excited magnetic nanoparticles produce a temperature increase of the tissue volume of less than 1° C., 0.75° C., 0.5° C., 0.4° C., 0.3° C., 0.2° C. or 0.1° C. Preferably also excited magnetic nanoparticles produce a temperature increase of the tissue volume of more than 1° C., 0.75° C., 0.5° C., 0.4° C., 0.3° C., 0.2° C. or 0.1° C.

Preferably, magnetic nanoparticles are excited by at least one cycle combining an excitation of magnetic nanoparticles producing a temperature increase of the tissue volume of more than 1° C. followed by an excitation of magnetic nanoparticles producing a temperature increase of the tissue volume of less than 1° C.

As intended herein, the temperature of the tissue volume can be measured using the standard thermometry method, which may involve the use of thermocouples, thermistors, resistance temperature detector, or infrared camera.

Direct treatment or destruction of the pathological cells in the individual may notably be due to the movements of the magnetic nanoparticles, which may for instance disrupt membranes or proteins, in particular of the extracellular matrix, or to the temperature increase, in particular above 1° C., more particularly the hyperthermia, produced by these magnetic nanoparticles.

Indirect treatment or destruction of the pathological cells in the individual may notably be due to destructions of blood vessels into the tissue volume or to the attraction of immune cells into the tissue volume.

As such, preferably blood vessel, arteria, or any type of channel carrying blood within the tissue volume are destroyed according to the invention.

As such also immune cells, in particular immune cells attracted by the immune attractant as defined above, are attracted into the tissue volume.

Preferably, upon excitation by radiation, immune cells involved in the destruction of the tissue volume may be activated and destroy pathological cells, either directly or by activating or releasing another immune substance such as antibody, interleukin, cytokine, chemical compounds that destroy the pathological cells, preferentially contained in non-heated tissue volume regions or in tissue volume regions not exposed to radiations.

Preferably, upon excitation by radiation, immune cells involved in the protection of the tissue volume, such as Treg cells, Th2 cells, myeloid cells, or macrophages of M2 phenotype, or immunosuppressive cytokines such as TGF-β, IL-10, VEGF, may be deactivated, destroyed, or their production or activity may be stopped or decreased. They may then not be able to prevent pathological cell destruction.

Indirect treatment or destruction of the pathological cells in the individual may notably be due to a by-stander effect, i.e. preferably an effect that induces the destruction of pathological cells more than 1, $10^2$, $10^3$, $10^4$, $10^5$, $10^6$, $10^7$, or $10^9$ nm away from the tissue volume, which is heated or exposed to radiation. It may also be due to an immune reaction or to a type of cell death, such as apoptosis or necrosis that either induces an immune reaction against the tumor or sends a message of self-destruction to the pathological cells, preferentially contained in non-heated tissue volume regions or in tissue volume regions not exposed to radiations.

EXAMPLES

Signification of Abbreviation

In DX, X means the day following administration of U87-Luc cells in the mouse brains in examples 2, 5, 6 and 10 or the day following administration of glucose or the different suspensions of nanoparticles in GL-261 subcutaneous tumors in examples 8 and 9; MS designates a magnetic session; in MSX, X denotes the number of magnetic session; in MX, X designates mouse number, MC designates chains of magnetosomes isolated from magnetotactic bacteria; M designates the central part of magnetosomes; M-PLL, M-PEI, M-CA, M-OA, M-Chi, M-Neri, M-CMD designate the central part of magnetosomes or magnetosome minerals coated with poly-L-lysine, polyethelyeneimine, citric acid, oleic acid, chitosan, neridronate, carboxymethyl-dextran, respectively; M-PNN designates MC or M-PLL co-localized with PNN, i.e. MC or M-PLL separated from PNN by a distance of less than 1 µm, AMF designates alternating magnetic field.

REFERENCES

Part of the materials and methods presented in this invention were previously described in two patents: i), FR1501267 filed Jun. 17, 2015 at INPI, France, entitled "Nonpyrogenic preparation containing nanoparticles synthesized by magnetotactic bacteria for medical or cosmetic applications" with PCT number PCT/FR2016/000095, filed Jun. 15, 2016 at INPI, France, ii), FR1502228 filed Oct. 21, 2015 at INPI, France, entitled "Particle comprising at least one ferrimagnetic iron oxide nanoparticle associated with at least one compound for medical or cosmetic application."

Example 1: Materials and Methods

FR1501267 (page 18 to 19) describes methods of characterization of the different nanoparticles, in suspension or not. These methods enable: i), determination of the iron concentration of the different nanoparticle suspensions, ii), observation of nanoparticles by transmission electron microscopy (TEM), iii), determination of the endotoxin concentration of the different nanoparticle suspensions using the Limulus Amebocyte Lysate test (LAL), iv), estimates of the percentages of Carbon, Hydrogen, Nitrogen, Sulfur (CHNS) in nanoparticles, v), measurements by diffusion of nanoparticle zeta potentials and/or hydrodynamic sizes, vi), assessment of the suspension stability by absorption. Nanoparticle characterization by Fourier transform infrared absorption method, FTIR, is described in International Journal of Pharmaceutics, Vol. 434, P. 444-452 (2012). Methods for measuring nanoparticle magnetic properties, including hysteresis cycle, ZFC and FC curves, are described in J. Phys. Chem C, V. 112, p. 12304 (2008). Nanoparticle specific absorption rate, SAR, measured in watts per gram of iron is estimated using the formula $SAR=C_V(\Delta T/\delta t)/C_{Fe}$, where $C_V=4.2$ J/gK is the water specific heat capacity, $(\Delta T/\delta t)$, measured in ° C. per second, is the slope at the origin of the variation of temperature with time and $C_{Fe}$, measured in mg of iron per ml, is the nanoparticle concentration. Cytotoxicity of the various nanoparticles is estimated using an MTT assay following a protocol described in ACSNano, V. 5, P. 6279-6296 (2011). Preparation and characterization of suspensions containing magnetosome chains isolated from AMB-1 magnetotactic bacteria, designated as MC, are described in patent FR1501267 (page 21 and in Tables 1 and 2, pages 43 and 44). When a MC suspension is deposited on a substrate and observed by TEM, we observe that magnetosomes tend to align in a long chain, leading to a homogenous magnetosome distribution. Magnetosomes have a cubo-octahedral geometry, a high level of crystallinity, a size that is larger than 20 nm for most magnetosomes, an average size of 45 nm, ferrimagnetic properties at physiological temperatures with a coercivity Hc of 200-300 Oe and a ratio between saturating magnetization and remnent magnetization Mr/Ms of 0.45. FTIR spectra, TEM and magnetic measurements of MC suggest that magnetosomes in MC are made of a core, composed of maghemite, surrounded by organic material that binds magnetosomes together in chains. Endotoxin concentration of MC in suspension is estimated as 18000-150000 EU per mg in iron per ml of MC suspension, zeta potential of MC is estimated as −26 mV at pH 7. For 2 µl of a suspension containing 40 µg in iron of MC, mixed in water and exposed to an AMF of frequency 202 kHz and average strength 25 mT during 10 minutes, SAR of MC is estimated as 57 $W/g_{Fe}$. Synthesis and characterization of magnetosomes synthesized by AMB-1 magnetotactic bacteria cultivated in the presence of 400 µM rhodamine B and then extracted from these bacteria, designated as MCR400, are described in example 1 of patent FR1502228 (pages 32 to 34). Preparation and characterization of BNF-Starch suspension, purchased from Micromod (Micromod reference: 10-00-102), are described in example 1 of patent FR1501267 (pages 20 to 21). When a BN-Starch suspension is deposited on top of a carbon substrate and observed by TEM, we observe that BNF-Starch aggregate more than MC. BNF-Starch zeta potential is 10 mV at pH 7. They are surrounded by synthetic hydroxyethyl starch instead of biological material for MC. BNF-Starch core size without coating is estimated by TEM as 20 nm, leading to ferrimagnetic properties at physiological temperatures, but with lower values of Hc of 5.4 Oe than for MC. For 2 µl of a suspension containing 40 µg of BNF-Starch mixed in water and exposed to the same AMF than with the MC, we measure a SAR of 10 $W/g_{Fe}$, lower than for the MC. Preparation and characterization of the central parts of magnetosomes isolated from MSR-1, designated by M, are described in example 3 of patent FR1501267, from pages 23 to 25 and in Tables 1 and 2. TEM measurements show that M tend to aggregate when they are deposited on a substrate and possess a small percentage in weight of carbon of 2.39%. M have a coercivity, Hc, of 10 mT, and are essentially composed of maghemite. LAL tests show that suspensions containing M have an endotoxin concentration of 10-100 EU per mg in iron per ml of M suspension. For 1 mg of M mixed in an agar gel and exposed to the same AMF as for MC and BNF-Strach, we estimate a SAR of 128 $W/g_{Fe}$. Furthermore, M are unstable in suspension since the absorbance of 1 mg of M at 480 nm decreases rapidly by 80% in 20 minutes. Preparation and characterization of the central parts of magnetosomes isolated from MSR-1 magnetotactic bacteria, coated with poly-L-lysine, designated as M-PLL, are described in example 5 of patent FR1501267, pages 26 to 28 and in tables 1 and 2. Absorbance at 480 nm of 1 mg of M-PLL in suspension decreases by less than 20% in 20 minutes, indicating improved stability of M-PLL compared with M. For 1 mg of M-PLL mixed in an agar gel and exposed to the same AMF as for M and BNF-Strach, we estimated a M-PLL SAR of 61 $W/g_{Fe}$, a value, which is lower than that of M. Endotoxin concentration of a M-PLL suspension, measured by the LAL test, is 80 EU per mg of iron per ml of suspension. Cytotoxicity studies, pyrogenicity and acute toxicity of M-PLL are presented p. 28 to 30 of patent FR1501267. Preparation and characterization of M-PEI (example 15), M-PLL (example 5), M-PEI (example 16), M-CA (example 8), M-OA (examples 8 and 9), M-Chi (example 6), M-Neri (example 14), M-CMD (example 7), are described in different examples of patent FR1501267. The properties and characterizations of BNF-Starch, M, MC, M-PEI, M-PLL, M-PEI, M-CA, M-OA, M-Chi, M-Neri, M-CMD are summarized in tables 1 and 2 of patent FR1501267. Protocol used for cell preparation to carry out in vivo experiments are described for MDA-MB231 cells in ACSNano, V. 5, p 6279-6296 (2011). Similar protocols are used for preparing U87-Luc and GL261 cells. In the different mouse treatments, mice are treated, fed and watered following ethical rules. Mice are euthanized by cervical dislocation when weight losses exceed 20%, or when signs of pain, unusual posture or prostration are observed or when tumor sizes are larger than 1000-2000 mm$^3$. In examples 2, 5 and 6, a cell suspension containing $10^5$ U87-Luc cells per microliter is inoculated in brains of nude CD-1 female mice of 20 g, 7 weeks old, purchased from Charles River. At day 0, D0, mice are anesthetized with a mixture of ketamine/xylazine. Mouse head is positioned in a stereotactic frame, a craniotomy is performed at fixed coordinates (0.2.0) and 2 µl of a suspension containing $2.10^5$ U87-Luc cells are administered at (0.2.2). In examples 2 and 5, tumors grow during 8 days and nanoparticle or glucose administration is carried out at D8 while in example 6, tumors grow during 5 days and nanoparticle or glucose administration is carried out at D5. In examples 2, 5 and 6, tumor surface temperature is measured over time during the various MS using an infrared camera (EasIRTM-2, Optophase) placed 20 cm above the coil. We measure using a thermocouple (IT-18, Physitemp, Clifton, USA) the temperature at the tumor cell administration site, which can be associated with the pathological site, in a dead mouse receiving 40 µg of MC or M-PLL. We find that this temperature is similar to that measured with the infrared camera, suggesting that during the various MS, surface temperature measured with the infrared camera is similar to the temperature at the tumor cell administration site. In examples 2, 5 and 6, to follow variation of tumor volume with time, tumor bioluminescence intensity (BLI) is measured using an IVIS Spectrum 10 minutes after intraperitoneal administration into each mouse of 2 mg of luciferin mixed with 100 µl of PBS and a relation between tumor BLI and tumor volume is determined. Survival times of the different mouse groups are expressed as averages±standard deviations, with indications of p-value estimates. Histological studies are carried out on brain sections of mice treated similarly to those of examples 2, 6 and 10 fixed with a 4% solution of paraformaldehyde, cut into transverse slices of 2 mm thick and embedded in paraffin. Sections of paraffin blocks, 4 µm thick, are deposited on glass slides and stained with hematoxylin-eosin (H&E) and/or Prussian blue to distinguish between healthy and tumor sites and to determine magnetosome location, polynuclearneutrophiles (PNN), healthy and tumor cells. In examples 2 and 6, the different sections studied by histology are designated as HMC6h and HMC72h for sections collected from mice euthanized 6 hours and 72 hours following intratumor administration of 40 µg of MC respectively, HMC0hB for those collected from mice receiving 40 µg of MC and euthanized just after one MS, HMC4hB for those collected from mice receiving 40 µg of MC and euthanized 4 hours following a first MS, HMC12hB for those collected from mice receiving 40 µg of MC and euthanized 12 hours following a first MS, HMC24h3B for those collected from mice receiving 40 µg of MC and euthanized 24 hours following 3 MS, HMPLL6h and HMPLL72h for those collected from mice euthanized 6 hours and 72 hours after intratumor administration of 500 µg of M-PLL, HMPLL5.5hB for those collected from mice receiving M-PLL and euthanized 5 hours and an half following a first MS, HMPLL24h3B for those collected from mice receiving 500 µg of M-PLL and euthanized 24 hours following a third MS, HBNF6h and HBNF72h for those collected from mice euthanized 6 hours and 72 hours following intratumor administration of 500 µg of BNF-Starch respectively, HBNF5.5hB for those collected from mice receiving 500 µg of BNF-Starch euthanized 5 hours and an half following a first MS, HBNF24h3B for those collected from mice receiving 500 µg of BNF-Starch euthanized 24 hours following a third MS.

Example 2: Magnetosome Chains Extracted from AMB-1 Magnetotactic Bacteria Introduced into U87-Luc Brain Tumors and Exposed to an AMF Lead to Full Tumor Disappearance At D8, 7 different groups of mice receive at the coordinates (0.2.2) 2 µl of the various solutions or suspensions containing either 5% glucose (groups 1 and 2), 40 µg in maghemite of MC (groups 3, 4, 5) or 40 µg in maghemite of BNF-Starch (groups 6 and 7). Groups 1, 3 and 6 do not undergo any further treatment after D8. After D8, groups 2 and 7 are exposed to 12 MS at D8 (MS1), D9 (MS2), D10 (MS3), D15 (MS4), D16 (MS5), D17 (MS6), D22 (MS7), D23 (MS8), D24 (MS9), D29 (MS10), D30 (MS11) and D31 (MS12). Groups 4 and 5 are exposed to MS1 to MS12 and to additional MS at D36 (MS13), D37 (MS14) and D38 (MS15). During each MS mentioned in this example, mice are exposed to an AMF of average strength 25 mT and frequency of 202 kHz during 30 minutes. For the different groups of mice, BLI is measured at D7, D14, D21, D28, D35, D42, D49 and D56. Untreated mice (group 1), mice exposed to 15 MS (group 2), mice receiving at D8 40 µg of MC (group 3) or 40 µg of BNF-Starch (group 6) are prone to an increase of their tumor volume after tumor cell implantation at D0. The average tumor volume increases from 30 mm$^3$ at D7 to 40 mm$^3$ at D28 (group 1), from 10 mm$^3$ at D7 to 160 mm$^3$ at D35 (group 2), from 5 mm$^3$ at D7 to 265 mm$^3$ at D35 (group 3), from 15 mm$^3$ at D7 to 60 mm$^3$ at D28 (group 6). Average tumor temperature of these mice, measured during the different treatments, do not vary. In addition, mice belonging to these groups are rapidly euthanized, between D28 and D42, due to weight losses exceeding 20%. Average survival time is also low and similar for these mice at 40.3±1.1 days (group 1), 39.4±2.3 days, p=0.938, (group 2), 46.4±2.3 days, p=0.028, (group 3), 36.8±1.1 days, p=0.053, (group 6). Signs of antitumor activity aren't observed among these mice. By contrast, for mice belonging to group 5, receiving 40 µg of MC in U87-Luc intracranial glioblastoma tumors of average volumes ~25 mm$^3$ followed by 15 MS, mean tumor volumes decrease first from 25 mm$^3$ at D7 down to 5 mm$^3$ at D14, then increase from 5 mm$^3$ at D14 to 70 mm$^3$ at D42. During the various MS, brain tumor temperatures increase by an average of 4° C. at D8 (MS1), 1.7° C. at D9 (MS2), 0.4° C. at D10, D15 and D16 (MS3 to MS5), and do not increase after D17. For a mouse with a typical behavior belonging to group 5, the variation over time of the tumor volume shows a series of oscillations, a decrease from 7 mm$^3$ at D7 to 2 mm$^3$ at D14, between MS1 and MS3, an increase from 2 mm$^3$ at D14 to 9 mm$^3$ at D21, between MS4 and MS6, followed by a decrease from 9 mm$^3$ at D21 to 2 mm$^3$ at D28, between MS7 and MS9, followed by an increase from 2 mm$^3$ at D28 to 9 mm$^3$ at D35, between MS10 and MS12, followed by a decrease from 9 mm$^3$ at D35 to 2 mm$^3$ at D42, between MS13 and MS15, followed by an increase from 2 mm$^3$ at D42 to more than 14 mm$^3$ at D45. These oscillations suggest that the application of the AMF leads to clear and repetitive anti-tumor activity. MS15 does not however prevent tumor regrowth. For mice belonging to group 5, anti-tumor efficacy does not seem sufficient to increase mouse survival time, which is of 46.5±1.7 days, p=0.015, similar to that of mice belonging to groups 1, 2, 3 and 6. The presence of a tumor of large-size in mice belonging to group 5 may require the administration of more than 40 μg of magnetosomes to lead to complete tumor disappearance. Mice belonging to group 4 are treated similarly to those of group 5, except that average tumor volumes are smaller at 1 mm³ at D7. In mice belonging to group 4, tumor gradually disappears following MS1 to MS15, leading to the complete tumor disappearance without tumor regrowth at D35. For a typical mouse belonging to group 4, the tumor volume decreases from 3 mm³ at D7 to 1 mm³ at D28 to 0 mm³ at D 42. Temperature variations during the different treatments are similar to those observed in group 5. For these mice, a mean survival time of 83.9±4.3 days (p<0.0001) is estimated, which is 42 days on average longer than that of the other groups. This high value is however an underestimate since mice are euthanized at D150 to carry out brain histological analysis. 40% of mice belonging to group 4 are still alive at D150. At D150, mice, which are still alive, are euthanized and slices of their brain are imaged by optical microscopy. These images indicate the absence of tumor or lesion, which suggests that these mice are completely cured. Mice receiving at the center of intracranial glioblastoma tumors 40 μg of BNF-Starch followed by 15 MS (group 7) behave differently from those belonging to groups 4 and 5. Indeed, tumor volumes of these mice increase continuously from 3 mm³ at D7 to 60 mm³ at D37. In addition, in group 7, animal mean survival time is estimated as 45.5±2.3 days (p=0.053), a similar value to that estimated for groups 1, 2, 3, 5 and 6, suggesting that intratumor administration of BNF-Starch, followed by multiple MS, does not trigger any anti-tumor efficacy. A histological study is carried out on animals treated similarly to those belonging to groups 1 to 7 and euthanized at various times after treatment. In mice treated similarly to those of groups 1 and 2, receiving glucose at D8, followed (or not) by MS, which are euthanized 6 or 24 hours following glucose administration or 6 hours after one MS or 24 hours after a third MS, optical microscopy images of histological sections of mouse brains show a well-defined tumor with an elliptical shape, located at one site without any sign of damage that could have resulted from glucose administration. Furthermore, the presence of polynuclear neutrophils (PNN), also called granulocytes, is not observed in these images. The same type of tumor is observed in mice treated in the same way as those of group 3, receiving at D8 2 μl of a suspension containing 40 μg of MC, euthanized 6 or 72 hours after MC administration. HMC6h and HMC72h show that approximately 50% of the tumor surface is brown, suggesting the presence of MC at this site. At 6 hours (HMC6h), magnetosomes and PNN are not separated by more than 1 μm, are therefore located at the same site and co-localized magnetosomes and PNN are designated as M-PNN. PNN alone or magnetosomes alone are not observed. 8% of M-PNN are observed in the ventricles, suggesting that M-PNN could carry MC outside of the tumor through the blood vessels of the ventricles. 92% of M-PNN are observed in the tumor or in its periphery. We estimate that there are 18413 M-PNN on average per mm² of tumor. At 72 hours (HMC72h), magnetosomes seem more scattered than at 6 hours. There aren't any M-PNN or PNN alone, suggesting that PNN disappear between 6 and 72 hours following MC administration. In these mice, necrosis or apoptosis is not observed. For mice treated similarly to those belonging to groups 4 and 5, receiving 2 μl of a MC suspension at D8, euthanized immediately after the first MS (HMC0hB), we observe that magnetosomes occupy only 8% of the tumor surface, that they are predominantly located at the tumor periphery and that the amount of M-PNN is 4800 M-PNN on average per mm² of tumor. 4 hours after the first MS (HMC4hB), PNN alone or magnetosomes alone aren't observed and there are approximately 12800 M-PNN per mm² of tumor. Half of M-PNN occupy 15% of the tumor. The other half is observed at the tumor periphery. Considering mice euthanized 12 hours after a first MS (HMC12hB), just after two MS (HMC0h2B), or 24 hours after three MS (HMC24h3B), about 90% of magnetosomes are located near or in the PNN, 10% of them are near or in U97-Luc tumor cells and PNN are observed near the M-PNN area, which suggests that PNN are attracted by the magnetosomes. A fraction of M-PNN occupies about 7% of the tumor area, while another M-PNN fraction is localized in the ventricles. We observe approximately 27852 M-PNN per mm² of tumor. In HMC24h3B, there are 5 areas containing U87-Luc cells of much smaller surfaces than tumor surfaces observed just after or 4 hours after a first MS, suggesting that after three MS, treatment acted, causing a splitting of the initial tumor area, located at one site into smaller tumor surfaces located at different sites. This antitumor behavior in HMC24hB is further characterized by the presence of sites containing U87-Luc cells in a state of necrosis or apoptosis with magnetosomes internalized in U87-Luc cells or located at the surface of these cells, i.e. magnetosomes are mainly not separated by more than 1 μm from U87-Luc cells. In HMC24h3B, magnetosomes are either located near or in PNN or near or in U-87-Luc cells, i.e. magnetosomes are mainly not separated by more than 1 μm from PNN or U87-Luc cells. They are also located near the ventricles and small tumor portions, i.e. magnetosomes are mainly not separated by more than 1 μm from ventricles and small tumor portions. Compared with mice receiving MC with or without MS, those treated similarly to groups 6 and 7, receiving 2 μl of a suspension containing 40 μg in iron of BNF-Starch and euthanized 6 hours after BNF-Starch administration, or receiving the same BNF-Starch suspension and euthanized 24 hours after a third MS display a significantly different behavior. Indeed, on the one hand, PNN are not observed in histological images of brain sections. On the other hand, histological images show a large and well defined tumor without necrosis, suggesting that application of three MS in the presence of BNF-Starch into the tumor does not induce any antitumor activity. Pharmacological antitumor effect due to MC or BNF-Starch cytotoxicity in the absence of heat does not seem to occur. Administration of MC or BNF-Starch without AMF application (groups 3 and 6) does not appear to induce any anti-tumor efficacy. Secondly, anti-tumor efficacy may be due to cell mechanical disruption under application of an AMF without heat production. The AMF may induce a magnetosome movement, which weakens cells or cell membranes, leading to their destruction. In the total absence of heat, such a mechanism is however unlikely to occur since mice belonging to group 7, receiving BNF-Starch and exposed to 15 MS without any increase in tumor temperature, do not display any decrease in tumor volume following MS. However, for mice belonging to groups 4 and 5, in which the tumors are first heated during 4 MS and then unheated during the 11 remaining MS, antitumor activity is observed during the 11 remaining MS. This suggests that when tumor tissue is first sensitized by heat, anti-tumor activity may be triggered by the application of an AMF, which does not produce any temperature increase. It should be noted that the probes that we use to detect the temperature is not sensitive enough to detect temperature increase at cellular level or below (organelle, cell nucleus, individual nanoparticle . . . ). It is therefore possible that temperature increase occurs at small scale, but it is not detected. Third, the mechanism responsible for tumor destruction involves the heat produced by MC under application of an AMF since the only groups of mice which display clear anti-tumor efficacy are groups 4 and 5 whose tumors are heated. Moreover, in example 6, we show that increasing the amount of heat produced within the tumor by administering a larger amount of 500 μg of magnetosomes instead of 40 μg in this example leads to a percentage of mice, which are fully cured of 100% instead of 40% in this example. This supports the idea that heat is necessary to produce tumor destruction. When tumor tissues are heated to 40-45° C. during 30 minutes, as in mice belonging to groups 4 and 5 during the first 4 MS, irreversible cell damage could occur, which may be caused by: i), a change in cell membrane integrity, fluidity or permeability, ii), cytolysis, iii), dysfunction of actin filaments, microtubules or mitochondria. Cell damage could also be associated with the inhibition of the replication of DNA or RNA synthesis, to denaturation of the DNA polymerase. Hyperthermia may also lead to inflammatory infiltrates near necrotic areas with the presence of several immune cells such as dendritic cells, natural killer cells, as well as B and T cells. In this example, we find that cells of the immune system, called polynuclear neutrophils (PNN), are located at the same site as the magnetosomes for a mouse euthanized 6 hours after MC administration without MS, euthanized 4 hours after one MS or 24 hours after three MS. However, PNN are not observed after administration of MC followed by MS or 72 hours after MC administration without MS. These results suggest that PNN gradually migrate in the site, where magnetosomes are located between 0 and 6 hours following MC administration. Later on, PNN leave this site or are destroyed in the absence of application of the AMF. In fact, it is likely that the organic material surrounding the inorganic magnetosome core, which is mainly composed of lipids, proteins and LPS, is responsible for the recruitment of PNN. Indeed, when BNF-Starch with similar iron oxide composition than the magnetosome crystallized core but devoid of any organic bacterial residues are administered to tumors, neutrophils are not observed in tumors. In fact, PNN located at the same site as the magnetosomes, called M-PNN, are observed during a longer period of time in the presence than in the absence of MS. The application of AMF could dissociate the organic material from the magnetosome mineral core, leading to the attraction and migration of neutrophils towards the magnetosomes. Furthermore, the presence of M-PNN next to the ventricles after treatment suggests that PNN may carry magnetosomes outside of the tumor through the ventricle blood vessels. This behavior agrees with the known neutrophil function, which is to get rid of organic substances of bacterial origin. Since PNN are observed in the tumor site and the mice used in this study have Toll-like receptors, they could be involved in the tumor destruction, a type of behavior that has previously been observed in mice bearing B16 tumors. However, this assumption is uncertain since 100% of mice bearing the same U87-Luc tumors and treated similarly than those of groups 4 and 5, but with less immunogenic magnetosomes containing an amount of endotoxins of 80 EU per mg per ml and 5% of organic carbon at the magnetosome surface, compared with 18 000-150 000 EU per mg per ml and 14% of organic carbon for the MC are completely cured despite of a lower number of PNN (example 6). This suggests a greater efficacy with less immunogenic magnetosomes and a lower amount of PNN. In mice belonging to example 6, tumors are heated to higher temperatures during longer times, suggesting that, if the immune system is involved in the destruction of the tumor, its antitumor activity may come from heat and not from the intrinsic magnetosome immunogenicity. Histological analysis suggests that magnetosomes only occupy a small part of the tumor surface after the first MS (7-15%). This suggests that the destruction of a small tumor portion by magnetosomes exposed to AMF may induce the destruction of the remaining tumor portions. This mechanism could be of immunological origin as described above, apoptotic since heat is known to promote apoptosis and death of tumor cells through this mechanism, or be the result of damages by heat to the blood vessels irrigating the tumor, a behavior which may occur in mice of groups 4 and 5 since magnetosomes are observed in the ventricles, near blood vessels. Previous experiments, carried out with 2-3 mg of smaller superparamagnetic iron oxide nanoparticles (SPION) of 15 nm, administered in RG-2 or T-9 tumors produces tumor heating to 43-47° C. during 30 minutes by applying an AMF. This treatment resulted in a 15 to 44-day survival time following tumor implantation compared with 8 to 14 days for untreated rats. Due to better magnetosomes heating properties compared with SPION, the amount of magnetosomes necessary to eradicate U87-Luc tumor in this example is 20 μg per $mm^3$ of tumor, lower than 60 μg per $mm^3$ of tumor used to produce an even less efficient anti-tumor activity in previous studies. We can conclude from this example that: i) it is possible to completely eliminate U87-Luc glioblastoma tumors implanted in the brain of mice by intratumoral administration of 40 μg in iron oxide of MC, followed by 15 MS during which a AMF frequency of 202 kHz and average strength 25 mT is applied, ii), the antitumor activity is probably not due to the MC cytotoxicity, iii), antitumor activity is triggered by the heat produced by MC as BNF-Starch administered at the same quantity as MC and exposed to the same MS do not produce any tumor temperature increase and do not induce any anti-tumor activity, iv) in the presence of MC, it is possible to induce anti-tumor activity by applying an AMF, which doesn't produce any temperature increase provided that the tumor has been heated beforehand, v), the more the tumor is heated, the higher the anti-tumor activity is (comparison between examples 2 and 6), vi), it is possible to have immune cells (neutrophils) migrate towards MC, expected to be due to the presence of organic material (endotoxins) at magnetosome surface, where this migration is enhanced by the application of an AMF, vii), since the tumor can be completely destroyed while magnetosomes only occupy a small percentage of tumor surface (10%), it is possible that indirect mechanisms are responsible (at least in part) for tumor destruction, such as immunogenic, apoptotic or due to the destruction of the blood vessels irrigating the tumor. In such indirect mechanism, tumor cells containing nanoparticles could induce the destruction of the other tumor cells not containing the nanoparticles.

Example 3: In Vitro Treatment of U87-Luc Cells Brought into Contact (or not) with MC and Exposed (or not) to a MS A suspension containing 40 μg in maghemite of MC is brought into contact with $10^3$, $5.10^3$, $10^4$, $5.10^4$, $10^5$ or $5.10^5$ U86-Luc cells and exposed (or not) to a MS during which an AMF of average strength 25 mT and frequency 202 kHz is applied during 30 minutes. The mixture is then incubated during 4 hours at 37° C. in the presence of 5% $CO_2$. 10 minutes before the end of incubation, 2 µl of luciferin at 20 mg/ml are added to the mixture producing luminescence of living cells whose BLI is measured using an IVIS spectrum. For cells alone, BLI of U87-Luc cells increases linearly with the number of cells from 0 a.u. in the absence of cells up to 1.5 $10^9$ a.u. in the presence of 5 $10^5$ cells. When U87-Luc cells are brought into contact with MC in the presence (or not) of a MS, BLI first increases linearly with the number of cells up to $10^5$ cells, then saturates beyond $10^5$ cells. BLI saturation may be due to MC that promote cell death. The linear coefficient of BLI increase with increasing cell number decreases from 2500 for cells alone down to 210 for cells brought into contact with MC and down to 7 for cells brought into contact with MC in the presence of a MS. From the values of these linear coefficients, we deduce that the number of living cells decreases from 100% for cells alone to 8.4% for cells brought into contact with MC and 0.3% for cells brought into contact with MC in the presence of a MS. BLI saturation is probably not due to magnetosome screening, since such screening should prevail when the ratio between the number of magnetosomes and the number of cells is the highest, i.e. at low cell concentration. In addition, there would be no reason why such effect would be enhanced in the presence of the AMF since magnetosome concentration remains the same in the presence (or not) of the AMF. Instead, this loss of linearity could be associated with cells being destroyed by MC in the presence (or not) of a MS inducing the death of other cells not directly destroyed by MC. An indirect mechanism of cell death could occur whereby cells destroyed by MC with or without MS emit a signal or release a toxin that induces the death of others cells not initially destroyed by MC.

Example 4: In Vitro Determination of the Type of Cellular Death (Apoptosis or Necrosis) when U87-Luc Cells are Brought into Contact (or not) with MC and Exposed (or not) to a MS U87-Luc cells are cultivated in 30 mm Petri dishes at a density of 500000 cells per dish and brought into contact with: a 5% glucose solution (treatment 1), a M-PLL suspension containing 1 mg of iron in 1 ml (treatment 2), a M-PLL suspension containing 1 mg of iron in 1 ml followed by a MS which maintains the temperature at 45° C. during 30 minutes (treatment 3). 12 hours following treatments, cells are washed twice with PBS, are harvested by trypsinization and are incubated with Annexin V and propidium iodide for apoptosis and necrosis detection respectively. Invitrogen kit V13241 is used. Using a flow cytometer, luminescence of the treated cells is excited at 488 nm and luminescence intensity is detected at 530 nm and 575 nm for apoptosis and necrosis detection respectively. Treatments lead to 99% of living cells and 1% of necrotic cells (treatment 1), to 40% of living cells, 34% of necrotic cells and 26% of apoptotic cells (treatment 2), to 10% of living cells, 27% of necrotic cells and 63% of apoptotic cells (treatment 3).

Example 5: Treatment of Intracranial U-87 Luc Tumors by Administration to these Tumors of 40 µg in Iron Oxide of MC Followed by 3 MS During which an AMF of Average Strength 25 mT and Frequency 198 kHz is Applied During 30 Minutes A group of 10 mice is treated similarly to group 4 of example 2, except that mice are exposed to three MS at D8, D9 and D10 instead of fifteen MS for group 4. For mice exposed to 3 MS, tumor volumes increase continuously following the three MS and average survival time is 41±1 days, similar to the average survival time observed among untreated mice. For 3 MS anti-tumor activity is not observed and it is therefore necessary to use more than 3 MS to remove the tumor.

Example 6: Full Disappearance of Intracranial U-87 Luc Tumors by Intratumor Administration of M-PLL Followed by AMF Application At D5, 6 different groups, containing 9 mice each, receive at the site of tumor cell implantation, 2 µl of different solutions or suspensions containing either 5% glucose (groups 1 and 2), 500 µg in iron of M-PLL (groups 5 and 6) or 500 µg in iron of BNF-Starch (groups 3 and 4). Groups 1, 3 and 5 do not undergo any further treatment. After D5, groups 2, 4 and 6 are exposed to 15 MS at D5, D6, D7, D12, D13, D14, D19, D20, D21, D26, D27, D28, D33, D34 and D35 for group 2, 20 MS at D5, D6, D7, D12, D13, D14, D19, D20, D21, D26, D27, D28, D33, D34, D35, D40, D41, D42, D47 and D48 for group 4, to 27 MS at D5, D6, D7, D12, D13, D14, D19, D20, D21, D26, D27, D28, D33, D34, D35, D40, D41, D42, D47, D48, D49, D54, D55, D56, D61, D62 and D63 for group 6. Each MS involves the application of an AMF of frequency 202 kHz and average strength 25 mT applied during 30 minutes. 4 mice of group 6 and 5 mice of group 4 receive a second administration of 200 µg in iron of M-PLL (group 6) and 200 µg in iron of BNF-Starch (group 4) at D47 due to tumor regrowth. Intracranial administration of suspensions containing M-PLL or BNF-Starch in glioblastoma tumors, followed or not by MS, is safe, since signs of toxicity are not observed in animals receiving these treatments. Untreated mice (group 1) and mice exposed to 15 MS (group 2) are prone to tumor volume increase following D0. The average tumor volume increases from 2 $mm^3$ at D0 to 200 $mm^3$ at D45 (group 1) and from 2 $mm^3$ at D0 to 180 $mm^3$ at D45 (group 2). Average brain tumor temperatures of these mice, measured during these MS, do not vary. In addition, mice belonging to these groups are rapidly euthanized, between D28 and D45, due to weight losses exceeding 20%. Average survival time is also quite low and similar for these mice at 44±2 days for group 1 and 44±1 days (p=0.662) for group 2. Signs of anti-tumor activity are not observed among these mice. For mice belonging to group 5, which receive M-PLL in intracranial U87-Luc tumors without AMF application, average tumor volume increases less rapidly than in mice of groups 1 and 2. This delay in tumor growth results in an average survival time of 114±7 days in these mice, which is higher than that of groups 1 and 2, indicating anti-tumor activity, which may be attributed to poly-L-lysine cytotoxicity. After having received the same suspension of M-PLL than mice belonging to group 5, mice of group 6 are exposed to MS. For these mice, average tumor volumes rapidly decrease from 1.5 $mm^3$ at D0 to 0 $mm^3$ at D42, resulting in total tumor disappearance in five mice without tumor regrowth or a decrease in tumor volumes from 1.5 $mm^3$ at D4 to 0.6 $mm^3$ at D30, then a tumor volume increase from 0.6 $mm^3$ at D30 to 1.5 $mm^3$ at D47 in 4 mice. Because of tumor regrowth in these four mice, M-PLL suspension was administered a second time at D47. After this second administration followed by 9 MS, tumor volume decreases from 1.5 $mm^3$ at D47 to 0 $mm^3$ at D68 and the tumor completely disappears in all mice belonging to group 6 at D68. After D4, tumor volume either decreases quickly to reach 0 $mm^3$ at D11 for a typical mouse or first decreases to 0.8 $mm^3$ at D11, then increases from 0.8 mm$^3$ at D11 to 1.6 mm$^3$ at D45 and then decreases again from 1.6 mm$^3$ at D45 to 0 mm$^3$ at D69 for another typical mouse. Average tumor temperature increases are 17.5° C. at D5 (MS1), 16.5° C. at D6 (MS2), 10° C. at D7 (MS3), 7° C. at D12, D13, D14, D19, D20, D21, D26, D27, D28, D33, D34 and D35 (MS4 to MS15), 2° C. at D40 (MS16). It then remains unchanged at D41, D42, D47, D48, D49, D54, D55, D56, D61, D62, D63 (MS17 to MS27) for M46, M48, M49, M50 and M51 or remains unchanged at D41 and D42 (MS17 and MS18), and increases as a result of M-PLL re-administration by 15° C. at D47, D48 and D49 (MS19 to MS21) and 8.5° C. at D54, D55, D55, D56, D61, D62, D63 (MS22 to MS27) for M47, M52, M53 and M54 mice. All these mice are still alive at D350. At D350, a treated mouse is euthanized and slices of its brain, located in the area of tumor cell implantation, are imaged by optical microscopy. The images of these slices reveal the absence of tumor or lesion, which suggests that these mice are totally cured. For mice of group 3, which receive BNF-Starch, tumor volumes continuously increase from 1.5 mm$^3$ at D0 to 200 mm$^3$ at D35. In addition, the mean survival time of these mice is estimated as 41±2 days (p=0.338), a value similar to that of groups 1 and 2, suggesting that intratumor administration of BNF-Starch does not lead to significant antitumor activity. For mice belonging to group 4 receiving the BNF-starch and exposed to MS, the average tumor volume increases from D0 to D50. 7 mice (M28, M30, M31, M32, M33, M34 and M36) are prone to tumor growth delay compared with mice of groups 1, 2 and 3. In 2 mice (M29 and M35), total tumor disappearance without tumor regrowth is observed. Average temperatures of brain tumors increase by 8° C. at D5 (MS1), 0° C. at D6, D7, D12, D13, D14, D19, D20, D21, D26, D27, D28, D33, D34, D35, D40, D41, D42 (MS2 to MS18), 5° C. at D47 (MS19) due to BNF-Starch re-administration and 0° C. at D48, D49, D54, D55, D56, D61, D62 and D63 (MS20 to MS27). 20% of these mice are still alive at D350 and average survival time is estimated at 125±43 days, significantly higher than in groups 1 and 2, but also lower than in group 6, indicating that anti-tumor activity is significant among these mice, but less pronounced than in group 5. We now turn to the histological analysis. First, for mice euthanized 6 hours after administration of M-PLL without MS, we observe that: i) PNN and M-PLL are located at the same site, designated as M-PNN, ii), M-PLL and PNN are not alone, iii), M-PNN occupy 100% of the tumor area, iv), there are no M-PNN outside of the tumor, v), there isn't any necrosis or apoptosis, vi) there are approximately 16000 M-PNN per mm$^2$ of tumor surface. Second, for mice euthanized 72 hours after M-PLL administration without MS, we observe that: i) there aren't any M-PNN or PNN alone, ii), M-PLL occupy 40% of the tumor, iii), M-PLL seem to be internalized in tumor cells, iv), 14% of M-PLL are in the ventricles and 76% of M-PLL are in the tumor, v), there isn't any necrosis or apoptosis. Third, for mice that receive M-PLL and are euthanized 5 h 30 following a first MS, we observe that: i) there aren't any PNN or M-PLL alone, ii), PNN and M-PLL are located at the same site, designated as M-PNN, and are located at the tumor outskirt, iii), M-PNN occupy 13% of the tumor, iv), 70% of M-PNN are in the tumor and 30% of M-PNN are in the ventricles, v), necrotic and/or apoptotic cells are observed within 17% of the tumor area, vi), M-PLL appear to be internalized in tumor cells, vii), there are 28000 M-PNN per mm$^2$ of tumor surface. Fourth, for mice euthanized 24 hours after a third MS, we observe that: i), there aren't any PNN or M-PNN in the brain, ii), M-PLL occupy 17% of the tumor, iii), M-PLL are located at tumor outskirt, iv), M-PLL appear internalized in tumor cells. Fifth, for mice euthanized 6 hours after BNF-Starch administration without MS, we observe that: i), there is no PNN, ii), BNF-Starch occupy 12% of tumor surface and are located at tumor center, iii), there aren't any BNF-Starch outside of the tumor, iv), BNF-Starch appear internalized in tumor cells, v), necrotic and/or apoptotic cells occupy 23% of the tumor. Sixth, for mice euthanized 72 hours following BNF-Starch administration, we observe that: i), there aren't any PNN, ii), BNF-Starch occupy 53% of the tumor surface, iii), BNF-Starch are located at the tumor outskirt, iv), BNF-Starch seem internalized in tumor cells, v), BNF-Starch are not located outside of the tumor, vi), necrotic and/or apoptotic cells occupy 4% of the tumor. Seventh, for mice euthanized 5 h 30 minutes after the first MS, we observe that: i), there isn't any PNN, ii), BNF-Starch occupy 10% of the tumor area, iii), BNF-Starch are located next to the tumor, iv), there aren't any BNF-Starch in the ventricles, v), BNF-Starch seem internalized in tumor cells. Eighth, for mice euthanized 24 hours following the third SM, we observe that: i) there isn't any PNN, ii), BNF-Starch occupy 27% of the tumor area, iii), BNF-Starch are near the tumor, iv) there aren't any BNF-starch in the ventricles, v), BNF-Starch seem internalized in tumor cells. We can conclude from this example that: i) it is possible to completely destroy U87-Luc tumors implanted in the brains of mice with one or two administration(s) of a suspension containing 500 μg in iron of M-PLL followed by MS, ii), M-PLL and PNN are located at the same site, i.e. separated by less than 1 μm, suggesting that M-PLL attract PNN, iii), antitumor activity is observed by applying the AMF in the absence of heat production provided that the tumor was previously heated, iv), the administration of M-PLL results in the appearance of M-PNN 6 hours following M-PLL administration where the number of M-PNN is higher in the presence (28161 M-PNN per mm$^2$ of tumor) than in the absence (15772 M-PNN per mm$^2$ of tumor) of MS, suggesting that the AMF increases the recruitment of PNN, iv), 72 hours after M-PLL administration in the absence of MS or in the presence of three MS, there are no PNN, suggesting that PNN disappear from the tumor (they are either destroyed or they migrate outside of the tumor) and the AMF can't reactivate them, probably due to the small amount of endotoxins at the M-PLL surface which is sufficient to cause a first neutrophil activation or excitation at 6 hours but not sufficient to cause a second neutrophil activation or excitation at 72 hours, v), 6 hours after M-PLL administration without MS, the amount of M-PNN is not much lower for M-PLL, at 15772 M-PNN per mm$^2$ of tumor, than for MC administration, at 18 413 M-PNN per mm$^2$ of tumor, whereas the amount of endotoxins is much larger in MC than in M-PLL suspensions, which may suggest that neutrophil activation or excitation is due to the gradual dissociation of endotoxins from M-PLL or MC at a dissociation rate, which is independent of the amount of endotoxin associated with the nanoparticles, vi), after administration of M-PLL, 12 hours after the first MS, 0 minute after the second MS, 24 hours after the third MS, it is possible to activate PNN and the amount of M-PNN is 27852 M-PNN per mm$^2$ of tumor while after administration of M-PLL, 24 hours after a third MS, it is not possible to activate the M-PNN, suggesting that when the amount of endotoxins at nanoparticle surface is higher, for MC, it is possible to activate neutrophils over a longer period of time by applying an AMF, possibly by dissociating endotoxins over a longer period of time in the presence of the AMF, vii), between 0, 4 and 12 hours following MC administration following the first MS, the amount of activated PNN increases from 4800 per mm² of tumor (0 hour) to 12800 per mm² of tumor (4 hours), to 27 852 per mm² of tumor (12 hours), suggesting that by applying the AMF, it is possible to obtain a progressive increase in PNN activation or excitation over time, which may be due to a gradual dissociation over time of endotoxins from MC, a behavior that is not observed when the AMF is applied between 6 and 72 hours following MC administration without MS, for which the number of M-PNN per mm² of tumor decreased from 18413 to 0, viii), 6 hours after M-PLL administration, the amount of M-PNN in the tumor decreases from 100% without MS to 70% in the presence of MS and 30% of M-PNN are in the ventricles following MS, which may suggest that the AMF produces M-PLL migration through the ventricles, possibly to remove M-PLL in the bloodstream, ix), anti-tumor activity leading to the total tumor disappearance is observed while M-PNN occupy 5 h 30 after a first MS or 24 hours following a third MS 70% and 17% of the tumor respectively, which suggests that partial occupancy of the tumor by M-PLL is sufficient to induce anti-tumor activity and therefore that an indirect mechanism occurs in which tumor cells directly destroyed by the treatment induce the destruction of the other tumor cells, ix), necrosis and/or apoptosis is observed in the presence of MS, suggesting that anti-tumor activity is due to the application of the AMF, x), M-PLL and BNF-Starch seem internalized in tumor cells, suggesting that internalization could play a role in antitumor activity, xi), in all conditions involving BNF-Starch administration, 6 or 72 hours following BNF-Starch administration without MS or 6 hours following BNF-Starch administration and a MS or 24 hours following BNF-Starch administration and a third MS, we don't observe PNN, suggesting that in the absence of endotoxins, PNN are not activated, xii), in the absence of PNN, BNF-Starch are not observed in the ventricles, which suggests that PNN may carry nanoparticles to the ventricles.

Example 7: Dissociation of a Substance from Ferrimagnetic Iron Oxide Nanoparticles (MCR400) Exposed to Radiation Three suspensions, containing either 400 μg/ml in iron oxide of MCR400, 125 μM of rhodamine B, or 400 μg/ml in iron oxide of MC mixed with 125 μM rhodamine B, are irradiated at doses between 0 and 1350 Gy using a Faxitron (160 kV, 6.3 mA without filter, 67.5 Gy/min). Luminescence intensity of suspensions containing rhodamine B alone or the supernate of the mixture of rhodamine B and MC do not vary or decrease when suspensions are irradiated. By contrast, when the MCR400 suspension is irradiated, the luminescence of its supernate, excited at 550 nm and detected at 576 nm, increases dramatically from 250 arbitrary units (a.u.) in the absence of irradiation to 600-950 a.u. in the presence of more than 250 Gy. These results suggest the dissociation of rhodamine B from MCR400 under irradiation. Moreover, emission wavelengths of the supernate of MCR400 and of rhodamine B free in solution remain unchanged at 576 nm, for the different radiation dose received by MCR400 or rhodamine B. This suggests that rhodamine B, free in solution or associated with magnetosomes, is not modified under irradiation. Increase in luminescence intensity of the supernate of the MCR400 suspension with irradiation is attributed to the dissociation of rhodamine B from MCR400 when MCR400 are irradiated. Similar behavior could potentially be observed with other substances than Rhodamine B such as immunogenic substances that could dissociate from magnetosomes under irradiation and cause a stimulation of the immune system.

Example 8: Treatment of GL-261 Tumors, Grown Subcutaneously Under the Skin of Immunocompetent Mice by Administering Suspensions Containing BNF-Starch and Montanide, MC, M-PEI and Poly-IC, Followed (or not) by the Application of an AMF of Frequency 198 KHz and Average Strength 9 mT Female "Black 6" mice are anesthetized with a ketamine/xélazine solution. 50 μl of a suspension containing 10⁵ GL-261 cells mixed in RPMI are administered subcutaneously on the right and left flanks of mice using a syringe. After induction of the subcutaneous tumors, animals are randomized in different groups. When tumor volumes reach 10 to 100 mm³, different suspensions are administered in one of the two tumors (right or left flank). The different suspensions of nanoparticles administered contain: i), 25 μl of BNF-Starch (Micromod: 10-00-102) at 20 mg/ml in iron mixed with 40 mg/mL of Montanide ISA51 (suspension 1), ii), 25 μl of MC at 20 g/ml in iron with an endotoxin concentration of 18000 to 150000 EU/mg/mL (suspension 2), iii), 25 μl of M-PEI at 20 mg/ml in iron with an endotoxin concentration below 50 EU/mg/mg mixed with 10 mg/mL of polyI:C (suspension 3). Groups 1 and 2 contain nine mice each and receive suspension 1 without MS (group 1) or with 15 MS (group 2). Groups 3 and 4 contain 7 mice each and receive suspension 2 without MS (group 3) or with 15 MS (group 4). Groups 5 and 6 contain 6 mice each and receive suspension 3 without MS (group 5) or with 15 MS (group 6). Each MS consists in the application of an AMF of average strength 9 mT and frequency of 198 kHz during 30 minutes. MS are applied three times a week during 5 weeks. We observe that: i), in groups 1 and 2, all tumors located at the non-administered flank reach 100 mm³ at D25 and tumor volume decreases to 0 mm³ are not observed, two tumors located in the administered flank increase to 100 mm³ between D5 and D10 and then decrease to 0 mm³ at D20 (group 1), one tumor located in the administered flank increases to 300 mm³ at D6, decreases to 0 mm³ at D27-D34 and then increases again to 250 mm3 at D43 (group 2) while other tumors of the administered flanks don't decrease to 0 mm³ in groups 1 and 2, suggesting partial antitumor activity in groups 1 and 2 in the administered flanks, where this activity is not enhanced by the application of the AMF, ii), in groups 3 and 4, a very similar behavior is observed between the administered and non-administered flanks in each mouse, i.e. in 2 mice of group 3 and 2 mice of group 4, both administered and non-administered tumor increase to 5-50 mm³ at D5-D10, then decrease to 0 mm³ at D15-D22, then remain at 0 mm³ between D22 and D75 and tumor disappearance is observed on both flanks, in 1 mouse of group 3, both administered and non-administered tumors do not reach 100 mm³ at D25 and tumor growth delay is observed on both flanks, In an mouse of group 4, the administered tumor does not reach 100 mm³ at D25 while the non-administered tumor does not grow, suggesting that the antitumor activity of the administered tumor can prevent the growth of the non-administered tumor, in 4 mice of group 3 and in 3 mice of group 4, nor tumor growth delay nor tumor disappearance is observed on both flanks, iii), in groups 5 and 6, a very similar behavior is observed between the left and right flanks, in 3 mice of group 5 and 1 mouse of group 6, administered tumors grow to 20-100 mm³ at D7-D22 and then decrease to 0 mm³ at D22-D40 while non administered tumors do not grow. Moreover, two groups of 10 mice receiving in GL-261 tumors of mean volumes 80 mm³ a suspension containing 25 μg in iron of M-PLL per mm³ of tumor or 25 μg in iron of BNF-Starch per mm³ of tumor are not prone to tumor growth delay or tumor disappearance during the month following the administration of the suspensions, suggesting that in groups 1 to 4, the presence of the immunogenic substance in suspensions 1 and 2 induces anti-tumor activity. During the various treatments and in particular during MS, we measure with a thermocouple and an infrared camera that the tumor temperature does not increase. We can conclude from this example that: i) tumor disappearance is observed when tumors receive either of suspension 1 to 3, suggesting that suspensions 1 to 3 lead to anti-tumor activity, ii), tumor disappearance or tumor growth delay is not more pronounced in the presence than in the absence of AMF application, suggesting that AMF application does not increase the anti-tumor activity, maybe due to a too weak applied AMF and/or to a too small quantity of administered nanoparticles, preventing a measurable tumor temperature increase, iii), treatments with MC or M-PEI and poly:IC lead to similar behaviors on both administered and non-administered flanks, suggesting the activation or excitation of an indirect mechanism of tumor destruction, such as an immune mechanism, in which anti-tumor activity at the site of MC or M-PEI and poly:IC induces anti-tumor activity in another site that can be remote from the first site, iv), the presence of an immunogenic substance seems needed to induce antitumor activity since similarly treated tumors with suspensions of BNF-Starch or non-immunogenic M-PLL do not display any anti-tumor activity. The nanoparticle residence time in tumor, i.e. the time during which nanoparticles can heat the tumor, is determined as 4 days for M-PLL and 1 day for BNF-Starch.

Example 9: Treatment of GL-261 Tumors, Grown Subcutaneously Under the Skin of Immunocompetent Mice by Administration of Different Suspensions Containing Either M-PLL or M-PLL Mixed with MPLA Followed (or not) by the Application an AMF 20 μl of a suspension containing 2.10⁶ GL261 cells are administered subcutaneously on the left flank of female "Black 6" mice at D0. After 15 days, when tumors reach 50 mm³ on average, mice are anaesthetized with Ketamine/Xylazine and 25 μl of different suspensions containing M-PLL at 20 mg/ml in iron (suspension 1), M-PLL at 20 mg/ml in iron mixed with 40 μg of MPLA (suspension 2) or 5% glucose (solution 3) are administered at the tumor center. Groups 1 and 2, containing 6 and 7 mice respectively, receive solution 3 at D0. Groups 3 and 4 contain 7 mice each and receive suspension 1 at D0. In groups 5 and 6, containing 6 and 8 mice each, mice receive suspension 2 at D0. Group 1, 3 and 5 are not treated after nanoparticle or glucose administration while group 2, 4 and 6 are exposed to 15 MS following administration. During MS, an AMF of average strength 30 mT and frequency 200 kHz is applied during 30 minutes and MS are carried out three times a week on anesthetized mice. During MS, tumor temperature is measured using a thermocouple and an infrared camera. It does not increase for groups 1, 2, 3 and 5 while it increases to an average of 43° C. in groups 4 and 6. We observe that: i) in group 1, all tumors reach 1000 mm³ at D25 and there is no tumor growth delay or tumor disappearance, ii), in group 2, 2 mice are prone to tumor growth delay with tumor volume below 500 mm³ at D25, iii) in group 3, 1 mouse is prone to tumor growth delay with a tumor volume below 500 mm³ at D25 and 1 tumor grows to 50 mm³ between D0 and D10 and then disappears at D20, iv), in group 4, 3 tumors are prone to tumor growth delay and have a volume of less than 500 mm³ at D25 and 1 tumor reaches 50 mm³ between D0 and D20 then disappears at D20, iv) in group 5, tumors of all mice reach 1000 mm³ at D25 and no tumor growth delay is observed, v) in group 6, 2 tumors are prone to tumor growth delay and have a volume below 500 mm³ at D25 and 1 tumor reaches 50 mm³ between D0 and D20 and then disappears at D20. We can conclude from this example that: i), antitumor activity is observed when tumors are exposed to the AMF without M-PLL administration, when M-PLL are administered without AMF application or when M-PLL are administered and the AMF is applied, the last situation leading to strongest anti-tumor activity, ii), treatment with M-PLL and MLA does not seem more efficient than that with only M-PLL, suggesting that combining an immunogenic substance and a nanoparticle does not necessarily increase the efficacy of destruction of the primary tumor, iii), in the presence of the AMF leading to tumor temperature increase, treatment appears more efficient than in the absence of AMF.

Example 10: Treatment of GL-261 Tumors, Grown Subcutaneously Under the Skin of Immunocompetent Mice by Administration of Suspensions Containing M-PLL or BNF-Starch Followed (or not) by the Application an AMF 100 μl of suspensions containing ~10⁷ cells are administered subcutaneously in the left flank of 6 to 8 weeks old C57/BL6 mice, anesthetized with isoflurane. 10 days after tumor cell implantation, at D0, when tumours reach 50 to 150 mm³, 6 groups, containing 10 mice each, are treated as follows: Group 1 receives an intratumor administration of 25 to 75 μl of a suspension containing 25 μg in iron of M-PLL per mm³ of tumor, where the M-PLL suspension is concentrated at 50 mg in iron per mL. M-PLL administration is followed by a series of 11 to 15 MS at D0, D2, D4, D7, D9, D11, D14, D16, D18, D21, D23, D25, D28, D30, D32. MS, which last 30 minutes, consist either in a first magnetic treatment during which intratumor temperature is maintained at 43-46° C. by applying an AMF of 198 kHz and strength varied between 11 and 27 mT or in a second magnetic treatment during which intratumor temperature can not reach 43-46° C. and an AMF of 198 kHz and strength of 27 mT is applied. Group 2 receives an intratumor administration of 32 to 65 μl of a suspension containing 25 μg in iron of M-PLL per mm³ of tumor, where the M-PLL suspension is concentrated at 50 mg in iron per mL. Group 3 receives an intratumor administration of 32 to 47 μl of a suspension containing 25 μg in iron of BNF-Starch per mm³ of tumor, where the BNF-Starch suspension is concentrated at 50 mg in iron per mL. BNF-Starch administration is followed by a series of 7 to 15 MS at D0, D2, D4, D7, D9, D11, D14, D16, D18, D21, D23, D25, D28, D30, D32. MS, which last 30 minutes, consist either in a first magnetic treatment during which intratumor temperature is maintained at 43-46° C. by applying an AMF of 198 kHz and strength varied between 22 and 31 mT or in a second magnetic treatment during which intratumor temperature can not reach 43-46° C. and an AMF of 198 kHz and strength of 27 mT is applied. Group 4 receives an intratumor administration of 20 to 50 μl of a suspension containing 25 μg in iron of BNF-Starch per mm³ of tumor, where the BNF-Starch suspension is concentrated at 50 mg in iron per mL. Group 5 receives an intratumor administration of 50 µl of a 5% glucose solution followed by 11 MS at D0, D2, D4, D7, D9, D11, D14, D16, D18, D21, D23. During each MS, a magnetic field frequency 198 kHz and average strength 27 mT was applied during 30 minutes. Group 6 receives an intratumor administration of 50 µl of a 5% glucose solution.

In group 1, the efficacy of a M-PLL suspension to eradicate subcutaneous GL-261 tumors using magnetic hyperthermia treatment is evaluated by administering M-PLL at the center of GL-261 glioma tumors and by exposing mice to a first MS during which an AMF of 198 kHz and strength 11 to 27 mT is applied during 30 minutes. For a mouse with a typical behavior, tumor temperature rapidly increases from 29° C. before AMF application to 46° C. after 2 minutes of application of an AMF of 19 mT and then saturates at 45° C. during the remaining 28 minutes of application of the same AMF. The SAR of 40 W/gFe, deduced from the initial slope of the temperature variation with time, $\Delta T/\delta t=0.24°$ C./Sec, is about 25% lower than the SAR measured in the gel. This difference could be due to the lower strength of the applied magnetic field or possibly to M-PLL aggregation within a part of the tumor following AMF application. Spatial temperature distributions, measured at the tumor surface with an infra-red camera shows that within 2 to 3 mm surrounding the tumor center, the temperature remains between 43 and 46° C. This behavior suggests that mild hyperthermia occurs within a mean volume of about 100 mm$^3$, close to the mean tumor volume of 80 mm$^3$. First MS is followed by 10 to 14 additional MS. The number of mice in which intratumor temperature can reach 43-46° C. by applying an AMF of 198 kHz and strength 11 to 27 mT decreases from 10 during the first MS at D0 down to 4 during the tenth MS at D21, remaining above 40% of the total number of mice. Due to the loss of heating efficacy and to tumor growth of more than 25% from two successive tumor size measurements, a second M-PLL administration at a quantity of 25 µg of M-PLL in iron per mm$^3$ of tumor is carried out in 4 mice. To examine antitumor efficacy on mice belonging to group 1, variations of the tumor volume were measured during the days following M-PLL administration and animal survival rates were estimated. Compared with mice belonging to group 2 receiving only M-PLL without AMF or those of groups 5 and 6 receiving glucose in the absence or in the presence of an AMF respectively, we observe that 5 mice belonging to group 1 are prone to tumor growth delay. In the remaining 5 mice, the tumor disappears completely at D2, D25, D7, D7 and D11. In these mice, trace of the tumor are not visible 250 days following M-PLL administration, suggesting that they are fully cured. For mice belonging to group 1, where M-PLL suspension is re-administered at D11, D14, D16 and D18, a decrease in tumor volume is observed during the days following re-administration without however yielding complete remission. These mice are euthanized at D25, D28, D30 and D44. For mice belonging to groups 2 and 5, which receive the M-PLL suspension without magnetic treatment or are exposed to the second magnetic treatment without M-PLL administration, tumor volumes increase continuously without any sign of anti-tumor activity, suggesting that the latter is due to M-PLL administration followed by MS and not solely to the M-PLL administration. Further support for anti-tumor activity is provided by survival rate estimates, which are 140±37 days for mice belonging to group 1, much longer than 12±2 days found for mice belonging to groups 2, 5 and 6. Optical images of tumor sections stained with Perls prussian blue for a mice receiving an intra-tumor administration of M-PLL without and with 1 MS and euthanized 6 hours following M-PLL administration reveal that: i), the percentage of M-PLL within the tumor (the surface occupied by M-PLL divided by the tumor surface) decreases from 41% without MS down to 21% with MS and, ii), the percentage of necrotic area (the surface occupied by necrotic areas divided by the tumor surface) within the tumor increases from 21% without MS up to 30% with MS. Similarly, for mice receiving M-PLL without or with MS and euthanized 72 hours following M-PLL administration, optical images reveal that: i), the percentage of M-PLL within the tumor decreases from 34% without MS down to 29% with MS and, ii), the percentage of necrotic areas within the tumor increases from 15% without MS up to 26% with MS. This suggests that AMF application reduces percentage of occupation of M-PLL in the tumor and increases the percentage of necrotic areas within the tumor. Outside of dense dark areas where M-PLL are located, iron possibly coming from M-PLL is not detected, suggesting that M-PLL are concentrated in part of the tumor. Necrosis may not be the only mechanism responsible for tumor cell death when mice are treated by M-PLL administration followed by multiple MS since the percentage of necrotic areas in the tumor is not higher for mice treated with M-PLL than for those receiving glucose. In the site outside of the tumor where M-PLL are administered and exposed to two MS, very few necrotic areas are observed, essentially located in the surrounding skin. No necrotic area is observed in fatty or muscle tissues surrounding the tumor, suggesting that the treatment does not induce any significant damage to healthy tissues surrounding the tumor. This behavior may be explained by the temperature distributions, which shows that temperatures above 43° C., possibly inducing tissue damages, are not measured outside of the tumor and by tumor cells being more sensitive to heat than normal cells at these temperatures.

In group 3, a suspension of BNF-Starch was also administered at the center of GL-261 glioma tumors and mice were then exposed to a first MS during which an AMF of 198 kHz and strength 22 to 31 mT was applied during 30 minutes. For a typical mouse receiving this treatment and belonging to group 3 (M29), tumor temperature, measured at tumor center, increased up to 44° C. following the application of an AMF of a higher strength of 22 to 31 mT than for M-PLL. The SAR deduced from the initial slope of the temperature variation with time, $\Delta T/\delta t=0.155°$ C./sec., was 26 W/gFe, also lower than that estimated for M-PLL, indicating less efficient heating with BNF-Starch than with M-PLL. Compared with M-PLL, the temperature distribution at tumor surface, measured 10 minutes after the beginning of the session, displays a lower average temperature spread across the tumor. Indeed, mild hyperthermia with temperatures above 43° C. was reached within 2 mm (<50 mm$^3$) surrounding the tumor center, i.e. within a lower percentage of tumor volume of 50% than with M-PLL. Between MS 2 and MS 10, the number of mice in which the intra-tumor temperature could reach 43-46° C. decreased more rapidly with the BNF-Starch, from 3 at MS 2 to 1 at MS 10, than with M-PLL where it decreased from 9 at MS 2 to 4 at MS 10. This behavior is observed despite the fact that the number of mice that received a second nanoparticle administration is larger for the BNF-Starch (6 mice) than for the M-PLL (4 mice). It can be concluded that increasing the magnetic field strength and the quantity of nanoparticles administered while using nanoparticles of lower SAR such as BNF-Starch does not necessarily enable to reach the same heating efficacy than that observed with nanoparticles of higher SAR such as M-PLL. Compared with mice receiving BNF-Starch (group 3) or glucose in the absence (group 6) or presence (group 5) of an AMF, tumor growth of 6 mice belonging to group 3 is delayed. Moreover, the tumor disappears fully in 2 mice at D14 and in 1 mouse at D23. The mean survival rate of mice belonging to this group is estimated at 69±30 days, a value which is larger than that of 10-14 days observed for the control groups but also much lower than that of 140±37 days obtained with M-PLL. It suggests that anti-tumor activity is observed with the BNF-Starch nanoparticles, but that this activity is less pronounced than that observed with M-PLL, a behavior that we attribute to a lower heating efficacy and different biodistribution properties for BNF-Starch than for M-PLL. Optical images of tumor sections stained with Perls prussian blue for a mice receiving an intra-tumor administration of BNF-Starch without and with 1 MS and euthanized 6 hours following BNF-Starch administration reveal that: i), the percentage of BNF-Starch within the tumor (the surface occupied by BNF-Starch divided by the tumor surface) increases from 122% without MS up to 144% with MS and, ii), the percentage of necrotic area (the surface occupied by necrotic areas divided by the tumor surface) within the tumor increases from 8% without MS up to 17% with MS. Similarly, for mice receiving BNF-Starch without or with MS and euthanized 72 hours following BNF-Starch administration, optical images reveal that: i), the percentage of BNF-Starch within the tumor increases from 53% without MS up to 93% with MS and, ii), the percentage of necrotic areas within the tumor increases from 7% without MS up to 43% with MS. This suggests that AMF application increases the percentage of occupation of BNF-Starch in the tumor and increases the percentage of necrotic areas within the tumor. As a whole, BNF-Starch appear to distribute more homogeneously than M-PLL in the tumor and the application of the AMF increases the percentage of BNF-Starch distribution within the tumor, whereas the opposite behavior is observed with M-PLL.

Example 11: Different Cytotoxicity Properties of M-PLL and BNF-Starch Incubated in the Presence of Healthy 3T3 and Cancerous GL-261 Cells During 24 Hours MTT cytotoxicity assay of nanoparticles incubated with GL-261 cells follows that described in ACSNano, V. 5, P. 6279-6296 (2011) for MDA-MB-231 cells while that of nanoparticles incubated with 3T3 cells follows ISO 10993-5 standard. Assays are carried out in the absence of radiation. Nanoparticle cytotoxicity on 3T3 cells (standard fibroblast cell line) is not observed for incubated suspensions containing M-PLL and BNF-Starch at concentrations in iron per mL of 87.5 µg/mL, 175 µg/mL, 250 µg/mL, 500 µg/mL and 1000 µg/mL. Indeed, in these cases, viability is always larger than 70% (ISO 10993-5: 2009 (E)). By contrast, when the same experiment is carried out on GL261 cells (tumor glioblastoma cells), cell viability is 70% for the M-PLL suspension incubated at 250 µg/mL and is reduced to 0% for M-PLL incubated at 500 µg/mL and 1000 µg/mL. Concerning BNF-Starch, cell viability is below 70% for BNF-Starch suspension incubated at 1000 µg/mL. We conclude from this example that M-PLL and BNF-Starch are more cytotoxic towards tumor (GL-261) than healthy (3T3) cells and therefore that the presence of nanoparticles both in healthy and tumor tissues can potentially selectively destroy tumor tissues without destroying healthy tissues.

Example 12: Comparison Between the Specific Absorption Rates of Suspensions of Chains of Magnetosomes Isolated from MSR-1 Magnetotactic Bacteria (MC) Mixed in Water, Uncoated Magnetosome Minerals (M) Mixed in Water, Magnetosome Minerals Coated with Citric Acid (M-CA) Mixed in Water To prepare the suspension of MC, MSR-1 magnetotactic bacteria with an optical density of 50 at 565 nm were mixed with KOH at 2M and the mixture was heated during 30 minutes at 80° C. under agitation at 150 rpm. MC were then selected magnetically by positioning a strong Neodinium magnet against the tube containing the mixture, by removing the supernate and by replacing it with PBS 10x. To prepare M, the suspension of MC was mixed with PBS and Triton and heated during one night at 50° C., the suspension was placed against a Neodinium magnet, the supernate was removed and replaced by phenol, the suspension was heated at 60° C. during two hours, the supernate was removed and replaced by chloroform, the supernate was again removed and replaced by sterile water. To prepare the suspension containing M-CA, 200 mg of citric acid monohydrate (33114, Sigma) were dissolved in 6 mL of ultrapure water. pH of the solution was adjusted to 6 with NaOH. Ultrapure water was added to the solution to obtain 10 mL of a solution at a concentration of 20 mg/mL and the solution was homogenized with a vortex. Under a sterile hood, the citric acid solution was filtered with a 0.45 µm filter. 630 µl of MC mixed in water at a concentration of 19 mg/mL were inserted in a 20 mL glass tube, the tube was positioned against a Neodinium magnet of 1.5 T, we waited until the supernate was transparent to remove the supernate. The supernate was replaced by 3.5 mL of an acid citric solution at 20 mg/mL at pH 6. Sterile apyrogen water was added to obtain 10 mL of a suspension of MC mixed with citric acid and water at a concentration in iron of 2 mg/mL. This suspension was placed in a sonicating bath (25 kHz) at 90° C. during 5 hours. The suspension was then washed twice by positioning the tube containing the suspension against the same Neodinium magnet and by replacing water with sterile water. The suspension was then centrifugated at 12 000 rpm during 30 minutes and the supernate was removed and replaced by sterile water. Suspensions containing in 0.5 mL of water 5 mg of MC (suspension 1), 5 mg of M (suspension 2), or 5 mg of M-CA (suspension 3) are exposed during 1000 seconds to an alternating magnetic field of average strength 25 mT and frequency 198 kHz. From the slope of the initial temperature variation with time, $\Delta T/\delta t = 1.1°$ C./sec. (suspension 1), $\Delta T/\delta t = 1.1°$ C./sec. (suspension 2), 2.2° C./sec. (suspension 3), we deduced SAR of 462 W/gFe (suspensions 1 and 2) and 924 W/gFe (suspension 3). For suspension 3, when the same experiment was carried out using 0.5 mg of M-CA mixed in 0.5 mL of water, we found a SAR of 226 W/gFe, indicating that the SAR decreases when it is measured at lower concentration. For suspension 3, when the same experiment was carried out using a suspension containing in 1.5 mL of water 15 mg of water, we found a SAR of 68 W/gFe, indicating that the SAR decreases when it is measured in a larger volume.

Example 13: Estimate of the SAR of BNF-Starch in Suspension as a Function of BNF-Starch Concentration and Strength of the Applied Alternating Magnetic Field 100 µl of suspensions containing various concentrations of BNF-Starch (1.4, 10, 14 or 20 mg in iron per mL) mixed in water are introduced in tubes of volume 250 μl and exposed to an alternating magnetic field of frequency 198 kHz and average strength of 25 mT or 30 mT. The thermocouple temperature probe is positioned at the bottom of the tube, we wait for 800 seconds that the temperature stabilizes before applying the alternating magnetic field during 15 minutes. For the average magnetic field strength of 25 mT, the measured SAR are 37 W/gFe at 1.4 mg/mL, 40 W/gFe at 10 mg/mL, 45 W/gFe at 14 W/gFe, 57 W/gFe at 20 mg/mL. For the average magnetic field strength of 30 mT, the measured SAR are 75 W/gFe at 1.4 mg/mL, 125 W/gFe at 10 mg/mL, 105 W/gFe at 14 mg/mL, 112 W/gFe at 20 mg/mL. We can conclude from this experiment that the SAR increases when the nanoparticle concentration increases. For the average magnetic strength of 25 mT, the concentration of 20 mg/mL does not seem to be sufficient to reach the maximum SAR since the SAR increases continuously as a function of concentration. By contrast, for the average magnetic field strength of 30 mT, the maximum SAR seems to be reached for the concentration of 10 mg/mL and the saturating concentration is between 1.4 mg/mL and 10 mg/mL. We can also conclude that the SAR increases with increasing magnetic field strength since for any given tested concentration, the SAR is larger for an applied magnetic field of strength 30 mT than for that of strength 25 mT.

Example 14: M, BNF-Starch, M-PLL, M-CA, M-OA Brought into Contact with GL-261 Cells in the Presence of an Alternating Magnetic Field of Frequency 198 kHz and Strength of 34 to 47 mT: Measurements of Nanoparticle Specific Absorption Rate, Cellular Internalization and Induced Cell Death To measure the specific absorption rate (SAR) of BNF-Starch, uncoated and coated magnetosome minerals, 1 mg/mL of these different nanoparticles is brought into contact with GL-261 cells and then exposed during 30 minutes to an alternating magnetic field of frequency 198 kHz and average field strength of 34 mT. The variation with time of the average spatial temperature distribution over the whole Petri dish containing the cells mixed with the various nanoparticles has been measured. From the initial slopes of the variations with time of the temperature, 0.018° C./sec.<ΔT/δt<0.047° C./sec., average SAR are estimated as 96 W/gFe, 73 W/gFe, 89 W/gFe, 141 W/gFe, 100 W/gFe, 196 W/gFe for M, BNF-Starch, M-PLL, M-CA, M-OA, and M-CMD, respectively. After 30 minutes of application of the alternating magnetic field, the maximum temperatures reached are also estimated as 39, 35, 34, 42, 42, and 51° C. for M, BNF-Starch, M-PLL, M-CA, M-OA, and M-CMD, respectively. While M-CMD, M-CA and M-OA lead to higher SAR values and maximum temperatures as well as to a more homogenous temperature distribution in the petri dishes than M, the opposite behavior is observed for M-PLL producing smaller SAR values and maximum temperatures as well as less homogenous temperature than M. This difference in behavior may be explained by different coating thicknesses obtained between the different coated magnetosome minerals. Indeed, the largest coating thickness of 6.4 nm, observed in M-PLL, leads to the lowest amount of heat produced. The presence of such thick coating could prevent M-PLL rotation or M-PLL friction with its viscus surrounding, hence minimizing the amount of heat produced by M-PLL movements. By contrast, magnetosome minerals with a thin coating seem to heat more, probably due to better dispersion, which favors homogenous nanoparticle distribution and possible nanoparticle movements in vitro. Optimal coating thickness, leading to enhanced heat production, appear to lie between 4 and 4.5 nm as it is the case for M-CMD and M-CA. As a whole, M-PLL, M-CA, M-OA, and M-CMD, all lead to higher SAR values and equivalent or better heat distribution than BNF-Starch, suggesting that they are all characterized by promising heating properties to carry out magnetic hyperthermia.

Next, we examine how efficiently M, BNF-Starch, M-CA, M-PLL, M-CMD, and M-OA can reach in vitro temperatures of 42-54° C., which are typical temperatures desired for magnetic hyperthermia. For that, 1 mg of the different nanoparticles is brought into contact with GL-261 cells and then exposed, or not for the control, to a heat treatment at 42-54° C. during 30 minutes. Heat is maintained at these temperatures by applying an alternating magnetic field of frequency 198 kHz and average strength of 34-47 mT, depending on the nanoparticle. While for M-CA, M-OA, and M-CMD, a magnetic field strength of 33 to 40 mT is applied to reach an average temperature in the Petri dish of 54° C. after 30 minutes of treatment, leading to a more homogenous temperature distribution than for M and BNF-Starch, a different behavior is observed for M-PLL that require the application of a higher magnetic field of 47 mT to reach an average temperature of 42° C. after 30 minutes of treatment and yield a less homogeneous temperature distribution than for M and BNF-Starch.

We now turn to a comparison between in vitro antitumor efficacy against GL-261 tumors of M-CA, M-PLL, M-CMD, and M-OA, with that of M and BNF-Starch. For all nanoparticles studied, the percentage of GL-261 living cells decreases in the presence of heat treatment at 42-54° C. under application of the alternating magnetic field. While for M-OA and M-CMD, GL-261 cell destruction appears to be the most efficient, leading to a decrease in the percentage of living cells of 30-40% following heat treatment, such decrease is only 15% for M-PLL, M-CA and M. For magnetic hyperthermia, it is desirable to use nanoparticles that can induce cell destruction at low magnetic field strength to prevent eddy currents. Therefore, M-OA and M-CMD seem to be the most efficient nanoparticles since their relatively high percentage of cell destruction of 30-40% is correlated with relatively high temperatures of 52-53° C. reached after 30 minutes of application of a magnetic field of relatively low strength of 33-40 mT. M-PLL and M appear to be the less promising nanoparticles since they induce the smallest percentages of cell destruction of 10-15%, obtained at relatively low temperatures of 42-48° C. by applying magnetic fields of a high strength of 47 mT.

To examine if in vitro antitumor efficacy is due to cellular internalization of the different nanoparticles, M-PLL, M-OA, M-CA, M-CMD, M, and BNF-Starch, are exposed to the same heat treatment as above at 42-54° C. The different nanoparticles are removed from the cell surface by washing and it is verified using an optical microscope that nanoparticle aggregates do not remain at the cell surface, so that the quantity of internalized nanoparticles, whether composed of crystallized or of dissolved iron, can be measured. After heat treatment, the amount of internalized iron either increases from 1 to 4 pg/cell for M-PLL, from 2 to 18 pg/cell for M-CA, or remains relatively unchanged at 0.5 to 4 pg/cell for M, M-OA, M-CMD and BNF-Starch. High cellular internalization of M-CA in the presence of the heat treatment at 54° C. may possibly be explained by M-CA high affinity for cellular membrane, as observed among other anionic maghemite nanoparticles with strong electrostatic interactions. On the one hand, M-CA that are prone to the highest level of internalization, produce a small decrease in the percentage of GL-261 living cells of only 10% following heat treatment at 54° C., which may be due to the relatively limited cytotoxicity of citric acid. On the other hand, nanoparticles that appear to yield most efficient cell destruction, i.e. M-OA and M-CMD don't internalize significantly in cells, suggesting that internalization may not in this case be the main factor responsible for nanoparticle cytotoxicity. Instead, in vitro antitumor efficacy following heat treatment by alternating magnetic field application may be due to aggregation of nanoparticles at the cell surface, which could result in cell lysis and/or to homogenous heating.

Example 15: Uncoated and Coated Magnetosome Minerals Brought into Contact with GL-261 Cells in the Presence, or not for the Control, of a Heat Treatment at 45° C. During 30 Minutes, Achieved by Applying an Alternating Magnetic Field of 198 kHz and Strength Adjusted to 34-47 mT: Estimates of Nanoparticle Specific Absorption Rates, Cellular Internalization and Cell Death 1 mg per mL of a suspension of M is brought into contact with GL261-cells and exposed to a first magnetic treatment during which an alternating magnetic field of frequency 198 kHz and average field strength 34 mT is applied during 30 minutes. Average temperature measured over the whole Petri dish containing the cells and M shows that it increases from 25° C. before application of an alternating magnetic field of 34 mT and 198 kHz to a maximum temperature of 35.3° C. following this treatment. From the initial slope of the average temperature variation with time, $\Delta T/\delta t=0.02°$ C./sec, SAR of M brought into contact with GL-261 cells is estimated as 86 $W/g_{Fe}$. Furthermore, in vitro anti-tumor efficacy of magnetic hyperthermia is estimated by measuring the decrease in the percentage of GL-261 living cells between the following two conditions: i), GL-261 cells are brought into contact during 30 minutes with 1 mg/mL in iron of M at 37° C. in the absence of magnetic treatment and ii), GL-261 cells are brought into contact with M as in i) and then immediately exposed during 30 minutes to an alternating magnetic field of frequency 198 kHz and average field strength of 47 mT that enables to reach an average temperature of 45° C. during treatment. Between conditions i) and ii), the percentage of living cells decreases from 94% down to 80%, whereas the quantity of M internalized per cell remains similar at 3.3 to 4.4 pg of iron per cell. The application of the alternating magnetic field leads to a decrease in the percentage of living cells but does not seem to enhance internalization, possibly due to the formation of aggregates.

Following the same protocol as for M-uncoated, i.e. by bringing into contact MC, M-PEI, M-Chi and M-Neri with GL-261 cells during 24 hours and by exposing these mixtures to the same first magnetic treatment, specific absorption rates and maximum temperatures are deduced as SAR~128 $W/g_{Fe}$, ~120 $W/g_{Fe}$, ~125 $W/g_{Fe}$ and ~72 $W/g_{fe}$ and as maximum temperatures of 39.9° C., 36.3° C., 36.8° C., 32.4° C., for MC, M-PEI, M-Chi, and M-Neri, respectively. Average SAR values and maximum temperatures are larger for MC, M-PEI and M-Chi than for M and M-Neri.

As for M, in vitro antitumor efficacy due to the application of the alternating field is studied by comparing the percentage of living cells in the following two conditions: i), when GL-261 cells are brought into contact with MC, M-PEI, M-Chi, M-Neri, in the absence of magnetic treatment and ii), when GL-261 cells are brought into contact with the same nanoparticles and exposed during 30 minutes to an alternating magnetic field of frequency 198 kHz and strength of 34 mT for MC, 35 mT for M-PEI, 43 mT for M-Chi, and 47 mT for M-Neri, to maintain the temperature of the mixtures at 45° C. during treatment. Between conditions i) and ii), the percentage of living cells is observed to decrease from 90% to 20% for MC, from 70% to 43% for M-PEI, from 85% to 75% M-Neri, from 95% to 77% for M-Chi. For condition i), the quantity of internalized coated magnetosome minerals is either relatively significant for M-PEI at 28 pg of iron per cell or low for MC, M-Neri, M-Chi at 1 to 1.8 pg of iron per cell. Between conditions i) and ii), the quantity of internalized nanoparticle remains either unchanged for M-Neri and M-Chi at 1 to 1.8 pg of iron per cell, increases for MC from 0.6 to 18 pg of iron per cell, or decrease for M-PEI from 28 pg to 10.4 pg of iron per cell. The most efficient nanoparticles, leading to the highest decrease in cell viability percentage of 70% following magnetic treatment, are MC, which are characterized by the highest SAR value of 128 $W/g_{Fe}$ and by the best heating homogeneity as well as by a large quantity of internalized magnetosomes of 18 pg of iron per cell following magnetic treatment. Less but still efficient nanoparticles, leading to a cell viability decrease of 20-30% after magnetic treatment are M-PEI and M-Chi. Their SAR value of 119-125 $W/g_{Fe}$ is lower than for MC and following magnetic treatment they are internalized either in a rather low amount at 1 pg per cell for M-Chi or in a rather large one at 12 pg per cell for M-PEI. The less efficient nanoparticles are M-Neri and M, which possess the lowest SAR value of 72-86 $W/g_{Fe}$ and a quantity of internalized nanoparticles of 2 to 4 pg of iron per cell resulting from magnetic field application. To reach a high efficacy of cell destruction, high SAR values, homogenous heating and nanoparticle internalization therefore seem required. In MC, M-PEI and M-Chi, superior heating properties compared with M and M-Neri could be explained by chain magnetic anisotropy leading to enhanced heating due to favored vibrations or rotations and possibly by the much thinner coating in M-PEI, M-Chi, and MC than in M-Neri, which may favor Brownian heating mechanism and thermal conductivity. In M-Neri and M-uncoated, the presence of a matrix surrounding the magnetosome minerals or of aggregates may prevent the physical rotation of the magnetosomes or thermally isolate them or both.

Interestingly, this study also provides insights about conditions of magnetosome internalization in the presence of an alternating magnetic field. For positively charged magnetosomes at pH 7, which are arranged in chains, such as M-PEI or M-Chi, enhanced internalization in the presence of an alternating magnetic field is not observed. In M-PEI, internalization, which is initially high in the absence of magnetic field application, even decreases after magnetic field application. Similarly, negatively charged magnetosomes at pH 7, which are not organized in chains, such as M and M-Neri, are not prone to cellular internalization. In M and M-Neri, aggregation or the matrix surrounding the magnetosome mineral core could prevent cellular internalization. The only magnetosomes that seem to internalize in the presence of the AMF are those, which are both negatively charged at pH 7 and arranged in chains, such as MC, suggesting that both of these conditions are required to yield internalization in the presence of the alternating magnetic field.

Example 16: Estimate of the SAR of M-CA, S-AC and MC Mixed in Suspensions at a Concentration of 10 mg/mL and Exposed to an Alternating Magnetic Field of 198 kHz and Average Strength 31 mT MC and M-CA were prepared as described in example 13. To prepare S-AC, 630 µl of a suspension containing 20 mg/mL of chemically synthesized nanoparticles (Iron (III) oxides sigma 544 884-5G) were mixed with 3.5 mL of a citric acid solution at 20 mg/mL and sonicated in a sonicating bath at 90° C. during 5 hours. The supernatant of the suspension was removed and replaced by water.

1 mg of MC, MC-A and S-A were mixed in 100 µl of water and exposed to an alternating magnetic field of 198 kHz and average strength of 31 mT. The SAR of each sample was deduced from the initial slope of the temperature variation with time as 669±134 $W/g_{Fe}$ for S-CA, 954±391 $W/g_{Fe}$ for M-CA, and 1234±307 $W/g_{Fe}$ for MC. We demonstrate here that magnetosome minerals coated with citric acid lead to a higher SAR value than their chemical counterpart. We also demonstrate that after removing bacterial residues from magnetosome mineral surfaces and recoating magnetosome minerals with citric acid, we obtain a SAR for M-CA, which is close to that of chains of magnetosomes (MC).

Example 17: Estimates of the SAR Per Tumor Volume (Date Summarized in Table 3)

The theoretical SAR (SAR (theo)) of MC, BNF-Starch, and M-PLL, expressed in watt per gram of iron contained in nanoparticle was measured by exposing suspensions containing 10 mg/mL of these magnetic nanoparticles contained in 100 µl of water to an alternating magnetic field of 200 kHz and 25 mT during 30 minutes. The SAR was estimated using the formula SAR=$C_v(\Delta T/\delta t)/C_{Fe}$, where $C_v$=4.184 J·K$^{-1}$·g$^{-1}$ is the specific heat capacity of water, $\Delta T/\delta t$ is the slope at the origin of the variation with time of temperature 2.568, 1.433 and 2.395 K/sec. respectively corresponding to MC, BNF-Starch and M-PLL, $C_{Fe}$=10 mg/mL is the concentration in iron of the different suspensions. We measured that SAR (theo)=1000 $W/g_{Fe}$ for M-PLL and MC and 600 $W/g_{Fe}$ for BNF-Starch.

A quantity of nanoparticles of 2.8 10$^{-5}$ $g_{Fe}$ for MC, between 5 10$^{-4}$ $g_{Fe}$ and 7 10$^{-4}$ $g_{Fe}$ for BNF-Starch, between 5 10$^{-4}$ $g_{Fe}$ and 7 10$^{-4}$ $g_{Fe}$ for M-PLL, was administered in intracranial U87-Luc glioblastoma of volumes 1 to 5 10$^{-3}$ cm$^3$ for MC, 1 to 2.5 10$^{-3}$ cm$^3$ for IONP, 6 10$^{-5}$ to 10$^{-3}$ cm$^3$ for M-PLL. Tumor volumes are designated by V. The magnetic nanoparticles were exposed to 1 to 27 magnetic sessions (MS1 to MS27) during which an alternating magnetic field of 200 kHz and 25 mT was applied during 30 minutes. After each magnetic session, the ratio between the surface occupied by the nanoparticles in the tumor and the tumor surface, which represented the percentage of nanoparticle in the tumor, was measured by histology. Before the first magnetic session, nanoparticles occupy 50%, 12% and 100% of tumor for MC, BNF-Starch and M-PLL respectively. The quantity of magnetic nanoparticles in the tumor, Q, was estimated by multiplying the percentage of nanoparticles in the tumor by the quantity of nanoparticles administered. The value of the experimental SAR, SAR (exp), was estimated using the formula SAR=$C_v(\Delta T/\delta t)/C_{Fe}$, where $C_v$=4.184 J·K$^{-1}$·g$^{-1}$ is the specific heat capacity of water, $\Delta T/\delta t$ is the slope at the origin of the variation with time of temperature (MS1: 0.0137 K/s, MS2: 0.0131 K/s, MS3: 0.095 K/s, MS4: 0.0067 K/s, MS5: 0.0047 K/s and MS6: 0 K/s for 28 µg of MC; MS1: 0.0112 K/s, MS2: 0.0037 K/s and MS3: 0 K/s for 500 µg of BNF-Starch; MS19: 0.0324 K/s and MS20: 0 K/s for 700 µg of BNF-Starch; MS1: 0.0799 K/s, MS2: 0.0380 K/s, MS3: 0.0188 K/s, MS4 to MS15: 0.0155 K/s, MS16: 0.0055 K/s, MS17: 0.0013 K/s and MS18: 0 K/s for 500 µg of M-PLL; MS19: 0.1249 K/s, MS20: 0.0947 K/s and MS3: 0 K/s for 700 µg of M-PLL), $C_{Fe}$ is the concentration in iron of the different suspensions (14 mg/mL for 28 µg of MC administered; 250 mg/mL for 500 µg of BNF-Starch or M-PLL administered; 350 mg/mL for 700 µg of BNF-Starch or M-PLL administered). The values of SAR (exp) are provided in table 3.

The variation of temperature after 30 minutes of application of the alternating magnetic field of 200 kHz and 25 mT, designated as $\Delta T$, was also measured.

The values of SAR(exp)·Q/V and SAR(theo)·Q/V for the different magnetic sessions was then also estimated.

TABLE 1

Properties of BNF-Starch, M-PLL, M-PEI, M-CA, M-OA, M-Chi, M-Neri, M-CMD.

| Properties of samples | | | | Coating Thickness (nm) | Iso-electric point (pH) | Hydrodynamic size of population (nm) | zeta potential (mV) | | | | | |
|---|---|---|---|---|---|---|---|---|---|---|---|---|
| Sample | Coating | Endotoxin (UE/mg/mL) | Species | | | | pH 2 | pH 4 | pH 6 | pH 8 | pH 10 | pH 12 |
| BNF-Starch | Starch | <50 | Chem. Synth. | 1-4 | 9.5 | 117 | 7 | 6 | 6 | 5 | −3 | −20 |
| MC | Bacterial residues | 18000-150000 | AMB-1 | 1-5 | 4.2 | 986 (81%) 4363 (14%) 176 (5%) | 20 | 2.5 | −18 | −26 | −34 | −38 |
| MC | Bacterial residues | 2000-170000 | MSR-1 | 1-5 | 6.4 | 2822 (82%) 535 (18%) | 15 | 14 | 3 | −15 | −26 | −31 |

TABLE 1-continued

Properties of BNF-Starch, M-PLL, M-PEI, M-CA, M-OA, M-Chi, M-Neri, M-CMD.

| Sample | Coating | Endotoxin (UE/mg/mL) | Species | Coating Thickness (nm) | Iso-electric point (pH) | Hydrodynamic size of population (nm) | zeta potential (mV) pH 2 | pH 4 | pH 6 | pH 8 | pH 10 | pH 12 |
|---|---|---|---|---|---|---|---|---|---|---|---|---|
| M | None | 20-100 | AMB-1 | 0 | 4.9 | 752 (97%) 5253 (3%) | 38 | 40 | −55 | −56 | −58 | −60 |
| M | None | 10-100 | MSR-1 | 0 | 3.5 | 3076 (79%) 677 (21%) | 18 | −8 | −1, 5 | −27 | −35 | −45 |
| M-PLL | Poly-L-lysine | 78 | MSR-1 | 4-16 | 8.7 | 2489 (92%) 137 (8%) | 43 | 35 | 24.5 | 5 | −14 | −34 |
| M-Chi | Chitosan | 25 | MSR-1 | 6 | 11 | 1908 (93%) 273 (7%) | 46 | 31 | 30 | 29 | 21 | −55 |
| M-CMD | Carboxy-méthyldextran | NA | MSR-1 | 2-20 | 3.4 | 5124 (6%) 1359 (79%) 331 (15%) | 20 | −8 | −25 | −30 | −31 | −31 |
| M-CA | Citric acid | 19 | MSR-1 | 1-15 | 3.7 | 788 | 25 | −12 | −18 | −27 | −31 | −38 |
| M-OA | Oleic acid | NA | MSR-1 | 0.5-5 | 3.5 | 123 | 30 | −10 | −40 | −50 | −55 | −60 |
| | | | | | | | NA | NA | −10 | −30 | −35 | −35 |
| M-Neri | Neridronate | NA | MSR-1 | 19-200 | 3.5 | 5560 (1%) 710 (59%) 207 (40%) | 40 | −7, 9 | −26 | −30 | −31 | −42 |
| M-PEI | PEI | NA | MSR-1 | 8-10 | 11 | 175 | 42 | 39 | 37 | 29 | 8 | −16 |
| M-PEI | PEI | <50 | AMB-1 | 4-18 | 11.3 | 1067 (93%) 5445 (1%) 125 (6%) | 50 | 44 | 35 | 26 | 12 | −10 |

TABLE 2

Number of mice with intratumoral heating of 43 to 46° C., SAR, maximum temperature reached during each session of AMF application, number of re-injected mice for mice belonging to group 1 (receiving M-PLL followed by AMF applications), group 3 (receiving BNF-Starch followed by AMF applications) and group 5 (receiving glucose followed by AMF applications). Treatment conditions are described in example 8. The residence time is estimated for more than 50% of mice with intratumor tumor temperature of 43 to 46° C. and one nanoparticle injection.

| Days of AMF application | Number of mice with intratumoral heating at 43-46° C. | SAR (W/g$_{Fe}$) | T$_{max}$ ° C. | Number of reinjected mice |
|---|---|---|---|---|
| Treatment M-PLL (group 1) | | | | |
| D 0 | 10 | 40.2 | 45.8 ± 1.5 | 0 |
| D 2 | 9 | | 44.9 ± 0.72 | 0 |
| D 4 | 6 | | 45.2 ± 0.76 | 0 |
| D 7 | 3 | | 46.1 ± 1.18 | 0 |
| D 9 | 1 | | 45.2 | 0 |
| D 11 | 1 | | 45.7 | 1 |
| D 14 | 2 | | 50.6 ± 7.9 | 1 |
| D 16 | 3 | | 45.7 ± 0.85 | 1 |
| D 18 | 4 | | 45.1 ± 0.46 | 1 |
| D 21 | 4 | | 44.7 ± 0.96 | 0 |
| D 23, D 25, D 28, D 30, D 32 | | | | 0 |
| Treatment BNF-Starch (group 3) | | | | |
| D 0 | 10 | 25.9 | 44.3 ± 0.56 | 0 |
| D 2 | 3 | | 45.1 ± 1.39 | 0 |
| D 4 | 5 | | 45.2 ± 2.1 | 4 |
| D 7 | 6 | | 45.3 ± 0.84 | 1 |
| D 9 | 6 | | 45.9 ± 1.7 | 1 |
| D 11 | 4 | | 44.4 ± 2.7 | 0 |
| D 14 | 2 | | 47.1 ± 7.2 | 0 |
| D 16 | 1 | | 46.5 | 0 |
| D 18 | 1 | | 44.2 | 0 |
| D 21, D 23, D 25, D 28, D 30, D 32 | | | | 0 |
| Treatment glucose 5% (group 5) | | | | |
| D 0, D 2, D 4, D 7, D 9, D 11, D 14, D 16, D 18, D 21, D 23 | 0 | 0 | | 0 |

TABLE 3

For the different tested nanoparticles (MC, BNF-Starch, M-PLL) exposed to different magnetic sessions, the theoretical SAR, quantity of nanoparticles administered in the tumor, the ratio between the surface occupied by the nanoparticles in the tumor and the tumor surface, Nanoparticle Surface/Tumor surface (%) deduced by histology measurements, the quantity of nanoparticles in tumor, Q, the experimental SAR, the temperature increase after 30 minutes of alternating magnetic field applications, ΔT, the theoretical SAR times Q divided by the tumor volume, the experimental SAR times Q divided by the tumor volume.

| Tested nano-particle | Magnetic session | SAR (theo) (W/gFe) | Quanity administered (gFe) | V: Tumor volume (cm³) | Nano-particle surface/ Tumor surface (%) | Q: Quantity of nanoparticles in tumor (g) | SAR (exp) (W/gFe) | ΔT (° C.) | SAR (theo).Q/V (W/cm³) | SAR (exp).Q/V (W/cm³) |
|---|---|---|---|---|---|---|---|---|---|---|
| MC | 1 | 1000 | 2.8E−05 | 1.0E−03 | 8 | 2.2E−06 | 4.00 | 4.00 | 2.24E+00 | 8.96E−03 |
|  |  |  |  | 5.0E−03 |  |  |  |  | 4.48E−01 | 1.79E−03 |
|  | 2 |  |  | 1.0E−03 | 15 | 4.2E−06 | 3.95 | 1.70 | 4.20E+00 | 1.66E−02 |
|  |  |  |  | 5.0E−03 |  |  |  |  | 8.40E−01 | 3.32E−03 |
|  | 3 |  |  | 1.0E−03 | 15 | 4.2E−06 | 2.87 | 0.34 | 4.20E+00 | 1.21E−02 |
|  |  |  |  | 5.0E−03 |  |  |  |  | 8.40E−01 | 2.41E−03 |
|  | 4 |  |  | 1.0E−03 | 15 | 4.2E−06 | 1.99 | 0.33 | 4.20E+00 | 8.36E−03 |
|  |  |  |  |  | 2 | 5.6E−07 |  |  | 5.60E−01 | 1.11E−03 |
|  |  |  |  | 5.0E−03 | 15 | 6.0E−06 |  |  | 1.20E+00 | 2.39E−03 |
|  |  |  |  |  | 2 | 8.0E−07 |  |  | 1.60E−01 | 3.18E−04 |
|  | 5 |  |  | 1.0E−03 | 15 | 6.0E−06 | 1.40 | 0.32 | 6.00E+00 | 8.40E−03 |
|  |  |  |  |  | 2 | 8.0E−07 |  |  | 8.00E−01 | 1.12E−03 |
|  |  |  |  | 5.0E−03 | 15 | 6.0E−06 |  |  | 1.20E+00 | 1.68E−03 |
|  |  |  |  |  | 2 | 8.0E−07 |  |  | 1.60E−01 | 2.24E−04 |
|  | 6 |  |  | 1.0E−03 | 15 | 6.0E−06 | 0.00 | 0.00 | 6.00E+00 | 0.00E+00 |
|  |  |  |  |  | 2 | 8.0E−07 |  |  | 8.00E−01 | 0.00E+00 |
|  |  |  |  | 5.0E−03 | 15 | 6.0E−06 |  |  | 6.00E+00 | 0.00E+00 |
|  |  |  |  |  | 2 | 8.0E−07 |  |  | 1.60E−01 | 0.00E+00 |
| BNF-Starch | 1 | 600 | 5.0E−04 | 1.2E−03 | 12 | 6.0E−05 | 0.19 | 8.24 | 3.00E+01 | 9.50E−03 |
|  |  |  |  | 2.5E−03 |  |  |  |  | 1.44E+01 | 4.56E−03 |
|  | 2 |  |  | 1.2E−03 | 50 | 2.5E−04 | 0.06 | 0.21 | 1.25E+02 | 1.25E−02 |
|  |  |  |  | 2.5E−03 |  |  |  |  | 6.00E+01 | 6.00E−03 |
|  | 3 |  |  | 1.2E−03 |  |  | 0.00 | 0.00 | 1.25E+02 | 0.00E+00 |
|  |  |  |  | 2.5E−03 |  |  |  |  | 6.00E+01 | 0.00E+00 |
|  | 19 |  | 7.0E−04 | 1.0E−03 | 2 | 1.4E−05 | 0.39 | 5.00 | 8.40E+00 | 5.46E−03 |
|  |  |  |  | 1.5E−01 |  |  |  |  | 5.60E−02 | 3.64E−05 |
|  | 20 |  |  | 1.0E−03 |  |  | 0.00 | 0.00 | 8.40E+00 | 0.00E+00 |
|  |  |  |  | 1.5E−01 |  |  |  |  | 5.60E−02 | 0.00E+00 |
| M-PLL | 1 | 1000 | 5.0E−04 | 7.0E−04 | 62 | 3.1E−04 | 1.34 | 17.61 | 4.43E+02 | 5.93E−01 |
|  |  |  |  | 1.8E−03 |  |  |  |  | 1.72E+02 | 2.31E−01 |
|  | 2 |  |  | 7.0E−04 |  |  | 0.64 | 16.67 | 4.43E+02 | 2.83E−01 |
|  |  |  |  | 1.8E−03 |  |  |  |  | 1.72E+02 | 1.10E−01 |
|  | 3 |  |  | 7.0E−04 | 25 | 1.3E−04 | 0.31 | 10.17 | 1.79E+02 | 5.54E−02 |
|  |  |  |  | 1.8E−03 |  |  |  |  | 6.94E+01 | 2.15E−02 |
|  | 4 to 15 |  |  | 6.0E−05 | 20 | 1.0E−04 | 0.26 | 6.83 | 1.67E+03 | 4.33E−01 |
|  |  |  |  | 1.0E−03 |  |  |  |  | 1.00E+02 | 2.60E−02 |
|  | 16 |  |  | 6.0E−05 |  |  | 0.09 | 2.00 | 1.67E+03 | 1.50E−01 |
|  |  |  |  | 1.0E−03 |  |  |  |  | 1.00E+02 | 9.00E−03 |
|  | 17 |  |  | 6.0E−05 |  |  | 0.02 | 0.11 | 1.67E+03 | 3.33E−02 |
|  |  |  |  | 1.0E−03 |  |  |  |  | 1.00E+02 | 2.00E−03 |
|  | 18 |  |  | 6.0E−05 |  |  | 0.00 | 0.00 | 1.67E+03 | 0.00E+00 |
|  |  |  |  | 1.0E−03 |  |  |  |  | 1.00E+02 | 0.00E+00 |
|  | 19 to 21 |  | 7.0E−04 | 6.0E−05 | 62 | 4.3E−04 | 1.49 | 14.83 | 7.23E+03 | 1.08E+01 |
|  |  |  |  | 1.0E−03 |  |  |  |  | 4.34E+02 | 6.47E−01 |
|  | 22 to 27 |  |  | 6.0E−05 | 25 | 1.8E−04 | 1.13 | 8.67 | 2.92E+03 | 3.30E+00 |
|  |  |  |  | 1.0E−03 |  |  |  |  | 1.75E+02 | 1.98E−01 |

The invention claimed is:

1. A method of treatment of a tissue volume comprising pathological cells in an individual, comprising:
administering to the individual an effective amount of a composition comprising magnetic nanoparticles to a first portion of a first tissue volume comprising pathological cells; and
intentionally exposing the magnetic nanoparticles to radiation and exciting the magnetic nanoparticles by the radiation for at least a first time, the radiation not consisting of only an alternating magnetic field with a strength between 0.001 mT and 100 T and a frequency between 1 KHz and 1000 kHz, the radiation to which the magnetic nanoparticles are intentionally exposed and by which the magnetic nanoparticles are excited comprising at least one radiation property selected from the group i) to v) consisting of:
i) a power between 0 and $10^9$ Watt or Watt per cm³ tissue volume,
ii) a frequency comprised between 0 and $10^4$ KHz,
iii) a power, strength, and/or frequency, which is/are sufficiently large to activate magnetic nanoparticles,
iv) a power, strength, and/or frequency, which is/are kept below a threshold to avoid toxicity, and v) an exposure time of at least $10^{-6}$ seconds, wherein only said first portion of said first tissue volume comprising pathological cells is occupied by the magnetic nanoparticles upon administration of the composition to the individual, and wherein the treatment affects said first portion of said first tissue volume comprising pathological cells to which the magnetic nanoparticles were administered and at least one of:

(a) a second portion of said first tissue volume comprising pathological cells to which the magnetic nanoparticles were not administered, said second portion of said first tissue volume being either exposed to the radiation or not exposed to the radiation; or (b) a second tissue volume comprising pathological cells, which is different from said first tissue volume and is not occupied by the magnetic nanoparticles, said second tissue volume being either exposed to the radiation or not exposed to the radiation.

2. The method of claim 1, wherein the magnetic nanoparticles in the first portion of the first tissue volume occupy less than 60% in volume of the first tissue volume.

3. The method of claim 1, wherein the first portion of the first tissue volume that the magnetic nanoparticles occupy is a peripheral portion of the first tissue volume comprising pathological cells.

4. The method of claim 1, wherein the magnetic nanoparticles have a specific absorption rate (SAR) upon their administration to the individual of at least $10^{-3}$ W per $cm^3$ of the first tissue volume.

5. The method of claim 1, wherein the magnetic nanoparticles have a specific absorption rate (SAR) upon their administration to the individual of $10^5$ W per $cm^3$ of the first tissue volume at the most.

6. The method of claim 1, wherein intentionally exposing the magnetic nanoparticles to radiation and exciting the magnetic nanoparticles by the radiation is performed at least another time, without re-administration of magnetic nanoparticles occurring after the at least a first time.

7. The method of claim 1, wherein at least one immune-attractant is releasably bound to the magnetic nanoparticles and is released upon excitation of the nanoparticles by the exposure to radiation.

8. The method of claim 1, wherein the magnetic nanoparticles are coated by a cytotoxic coating.

9. The method of claim 1, wherein the magnetic nanoparticles are iron oxide nanoparticles.

10. The method of claim 1, wherein the magnetic nanoparticles intentionally exposed to and excited by the radiation produce a temperature increase of the second tissue volume of less than 1° C.

11. The method of claim 1, wherein the first tissue volume comprising pathological cells is a tumor or a primary tumor.

12. The method of claim 1, wherein the composition is a pharmaceutical composition, a medicament or a medical device.

13. The method of claim 1, wherein said first portion of said first tissue volume to which the magnetic nanoparticles were administered and intentionally exposed to and excited by the radiation is located:

i) at a distance from said second portion of said first tissue volume that is smaller than a distance separating said first tissue volume from said second tissue volume, or ii) at a distance between 1 nm and 1 m from either (a) said second portion of said first tissue volume comprising pathological cells to which the magnetic nanoparticles were not administered nor excited by radiation or (b) said second tissue volume comprising pathological cells.

14. The method of claim 1, wherein the magnetic nanoparticles have at least one magnetic nanoparticle property selected from the group consisting of:

i) a coercivity, Hc, which is larger than $10^{-4}$, $10^{-3}$, $10^{-2}$, $10^{-1}$, 1, 10, $10^2$, $10^3$, $10^4$, or $10^5$ Oe;

ii) a ratio between remanent and saturating magnetization, Mr/Ms, which is larger than 0.001, 0.01, 0.1, 0.2, 0.3, 0.4, 0.5, 0.6, 0.7, 0.8, or 0.9;

iii) a saturating magnetization, Ms, which is larger than 0.1, 1, 10, or 100 emu/g;

iv) a non-zero magnetic moment and/or a stable magnetic moment;

v) diamagnetic, superparamagnetic, ferromagnetic or ferrimagnetic magnetic property; and vi) non-pyrogenicity.

15. The method according to claim 14, wherein the Hc, the Mr/Ms, and/or the Ms is or are measured at a higher temperature than 0, 0.1, 1, 2, 5, 10, 100, 200, 300, 400, 500, 700, or 1000 K.

16. The method of claim 1, wherein the magnetic nanoparticles comprise at least 1, 10, $10^2$, $10^3$, $10^4$, $10^5$, $10^6$, $10^7$, $10^8$, or $10^9$ magnetic or metallic atom(s) selected from the group consisting of iron, zinc, manganese, cobalt, and nickel.

17. The method of claim 1, wherein the magnetic nanoparticles are organized in chains of more than 2 magnetic nanoparticles.

18. The method of claim 1, wherein the magnetic nanoparticles are synthesized by living organisms.

19. The method of claim 1, wherein intentionally exposing the magnetic nanoparticles to the radiation and exciting the magnetic nanoparticles by the radiation has an effect selected from the group consisting of:

i) movement of the magnetic nanoparticles;

ii) production of heat by the magnetic nanoparticles;

iii) release of a substance bound to the magnetic nanoparticles; and iv) production of free radicals.

20. The method of claim 1, wherein the magnetic nanoparticles intentionally exposed to and excited by the radiation produce a temperature increase of the first tissue volume of more than 0.1° C.

21. The method of claim 1, wherein the pathological cells consist of or comprise an entity selected from the group consisting of:

i) cancer cells, ii) tumor cells, iii) viruses, iv) bacteria, and v) combinations thereof.

22. The method according to claim 1, wherein the treatment affects said first portion of said first tissue volume and at least one of (a) said second portion of said tissue volume or (b) said second tissue volume because of a condition selected from the group consisting of:

i) immune cells being attracted into the first tissue volume, ii) immune cells of the first tissue volume involved in destroying cells being activated and destroying pathological cells in the first tissue volume, iii) immune cells of the first tissue volume involved in protecting tissue being de-activated or destroyed, and iv) an immune reaction or a cell death that either induces an immune reaction against a tumor or sends a message of self-destruction to pathological cells contained in a region of a tissue volume that is not heated or is not exposed to the radiation.

23. The method according to claim 1, wherein the radiation to which the magnetic nanoparticles are intentionally exposed and by which the magnetic nanoparticles are excited is selected from the group consisting of:
  i) sound waves,
  ii) laser radiation,
  iii) ionizing radiation,
  iv) sound radiation,
  v) ultra-sound,
  vi) radiofrequencies,
  vii) moving alpha, beta, gamma, X-ray, neutron, proton, electron, ion, muon, meson, photon particles, and
  viii) moving particles with a weight.

24. The method of claim 1, wherein at least one of the second portion of said first tissue volume is exposed to radiation or said second tissue volume is not exposed to radiation.

25. The method according to claim 1, wherein the second tissue volume comprising pathological cells is a tumor or a tissue that is different from a primary tumor.

* * * * *